United States Patent [19]

Chow et al.

[11] Patent Number: 4,527,724

[45] Date of Patent: Jul. 9, 1985

[54] DISPOSABLE LINEAR SURGICAL STAPLING INSTRUMENT

[75] Inventors: Hector Chow, Cincinnati; Hugh Melling, West Chester, both of Ohio

[73] Assignee: Senmed, Inc., Cincinnati, Ohio

[21] Appl. No.: 503,231

[22] Filed: Jun. 10, 1983

[51] Int. Cl.³ .............................................. A61B 17/04
[52] U.S. Cl. .................................... 227/8; 128/334 R; 227/19; 227/DIG. 1
[58] Field of Search .............. 128/334 R, 334 C, 335; 227/8, 19, DIG. 1, 83, 156

[56] References Cited

U.S. PATENT DOCUMENTS

| | | | |
|---|---|---|---|
| 3,080,564 | 3/1963 | Strekopitov et al. | 227/DIG. 1 |
| 3,252,643 | 5/1966 | Strekopitov et al. | 227/109 |
| 3,275,211 | 9/1966 | Hirsch et al. | 227/124 |
| 3,315,863 | 4/1967 | O'Dea | 227/19 |
| 3,494,533 | 2/1970 | Green et al. | 227/DIG. 1 X |
| 3,589,589 | 6/1971 | Akopov | 227/153 |
| 3,692,224 | 9/1972 | Astafiev et al. | 227/DIG. 1 X |
| 3,795,034 | 3/1974 | Strekopytov et al. | 227/DIG. 1 |
| 3,935,981 | 2/1976 | Akopov et al. | 227/19 |
| 3,949,923 | 4/1976 | Akopov et al. | 227/19 |
| 4,296,881 | 10/1981 | Lee | 227/30 |
| 4,354,628 | 10/1982 | Green | 227/19 |
| 4,383,634 | 5/1983 | Green | 227/19 |

Primary Examiner—Paul A. Bell
Attorney, Agent, or Firm—Frost & Jacobs

[57] ABSTRACT

A disposable linear surgical stapling instrument comprising a body with handle means and trigger means and, at its forward end, a fixed anvil-supporting jaw. A movable jaw comprising a staple cartridge is mounted on the body and is operatively connected to the handle means and trigger means. An adjustment bolt is slidably mounted in the body and is shiftable forwardly and rearwardly therein by an adjustment knob rotatively mounted at the rearward end of the body. The adjustment bolt, when shifted forwardly, shifts the handle means and trigger means forwardly and the movable jaw toward the fixed jaw, the staple cartridge approaching the anvil. A staple driver is connected to and shiftable by the trigger means to drive staples from the cartridge, through the tissue to be sutured and against the anvil over a range of distances between the anvil and the cartridge constituting the working gap of the instrument. The adjustment bolt also actuates indicator means to each side of the instrument indicating when the working gap has been achieved. An alignment pin is mounted on the body, extending through the cartridge, and is shiftable to an operative position extending into the fixed jaw. Safety means prevents rotation of the adjustment knob unless the alignment pin is in its operative position. Another safety means prevents actuation of the trigger means until the distance between the anvil and cartridge approaches the working gap. Additional means locks the trigger means after achieving its actuated position to give visual, tactile and audible indication that the staples have been formed and implanted.

22 Claims, 45 Drawing Figures

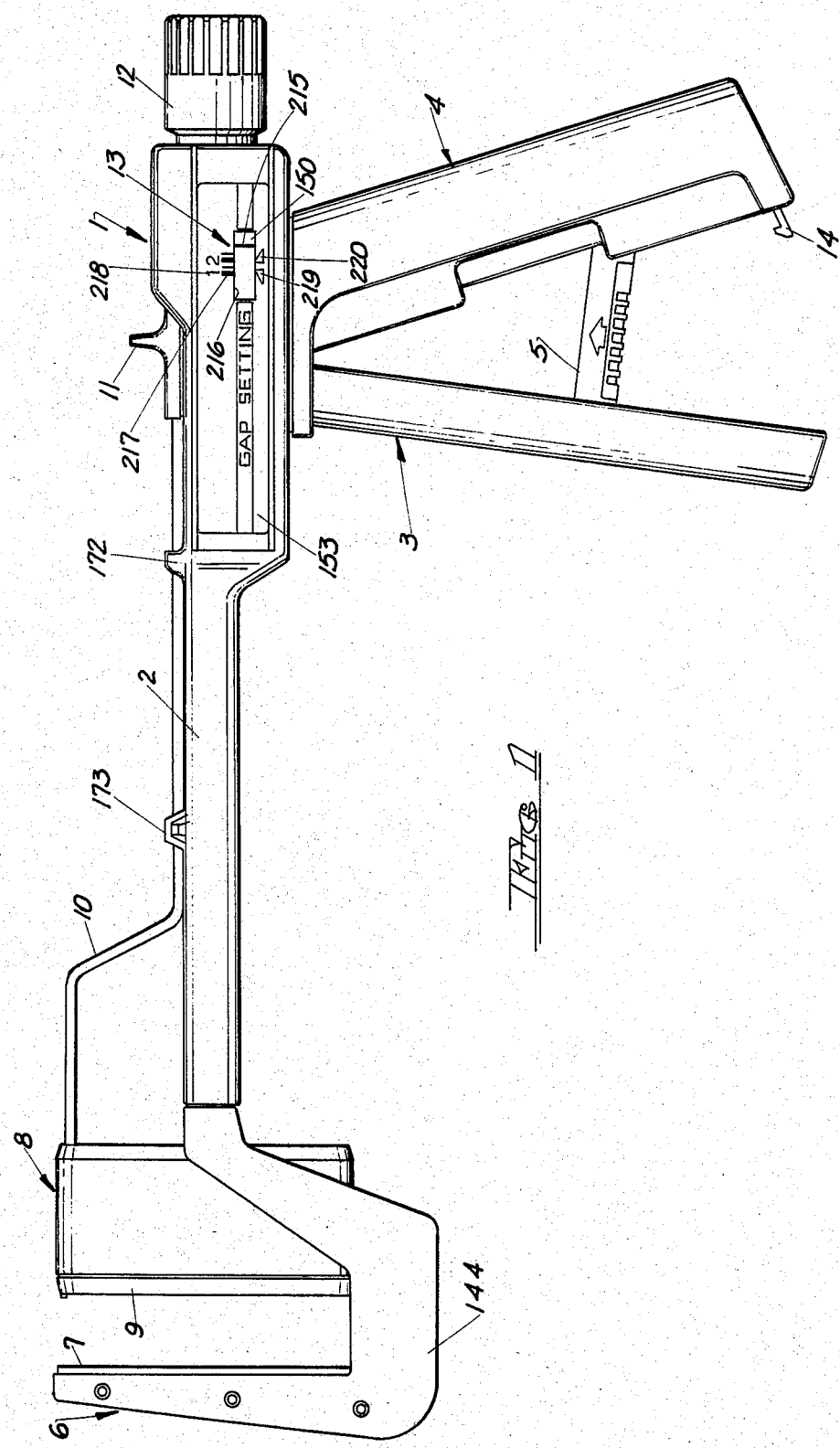

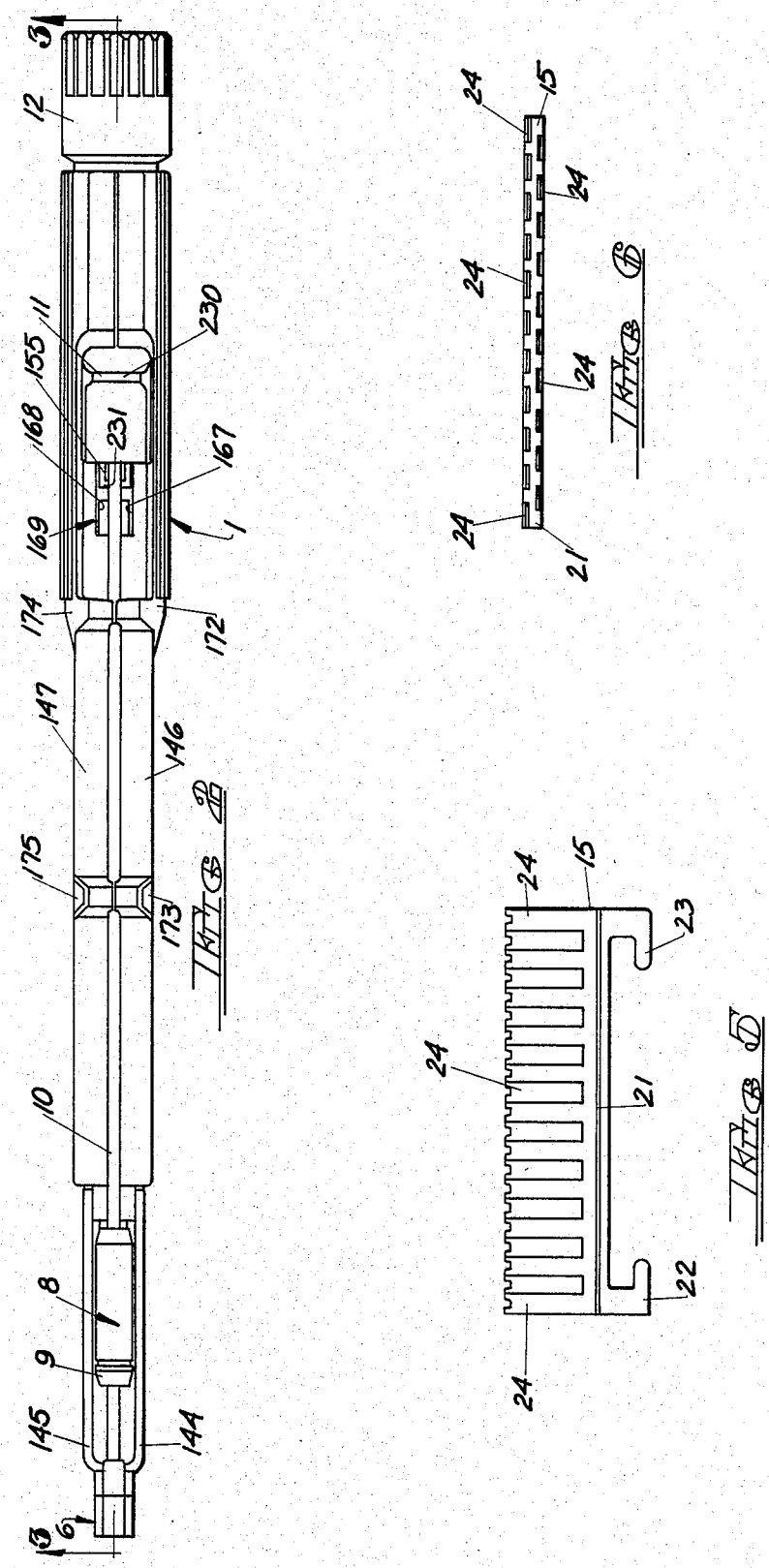

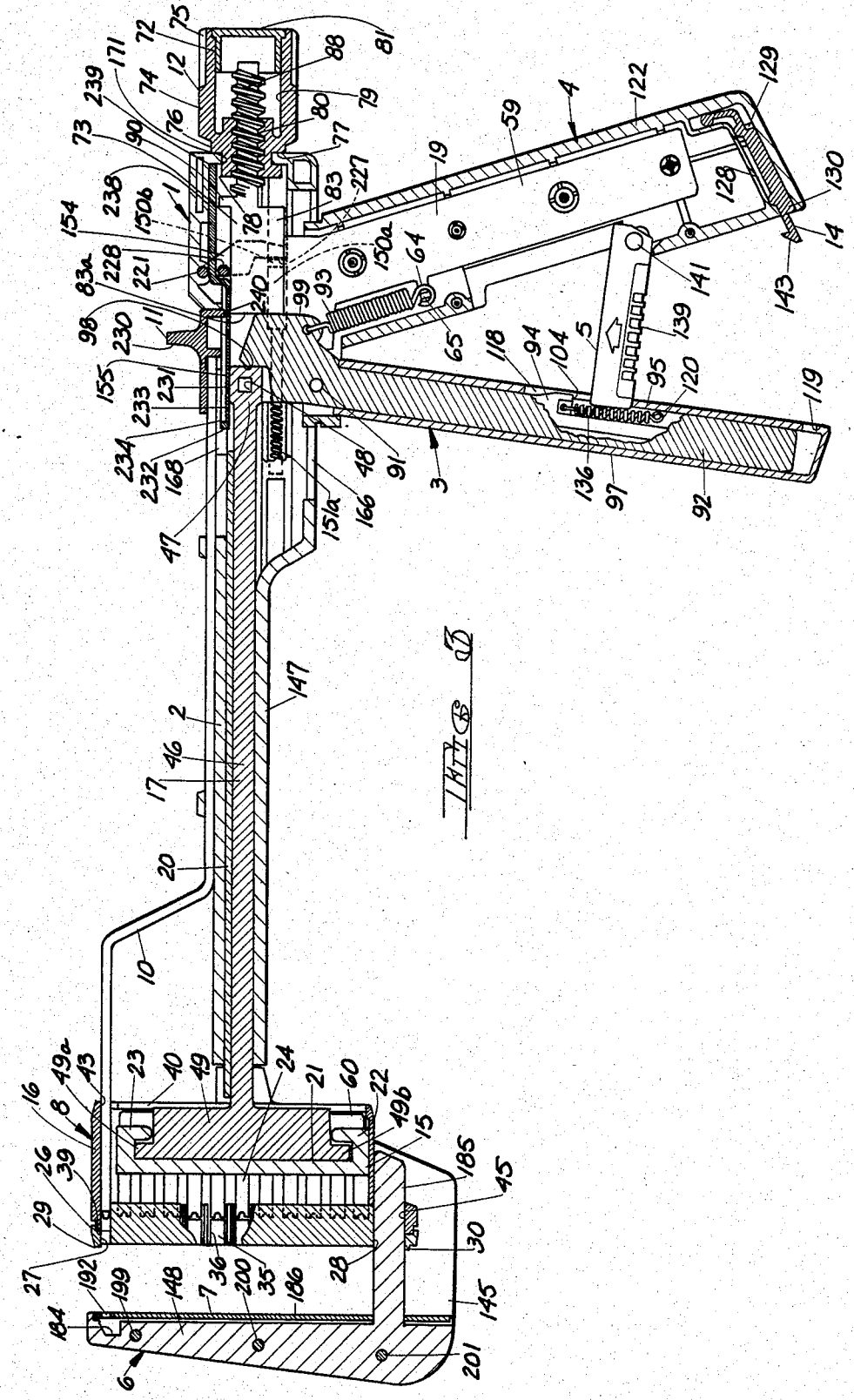

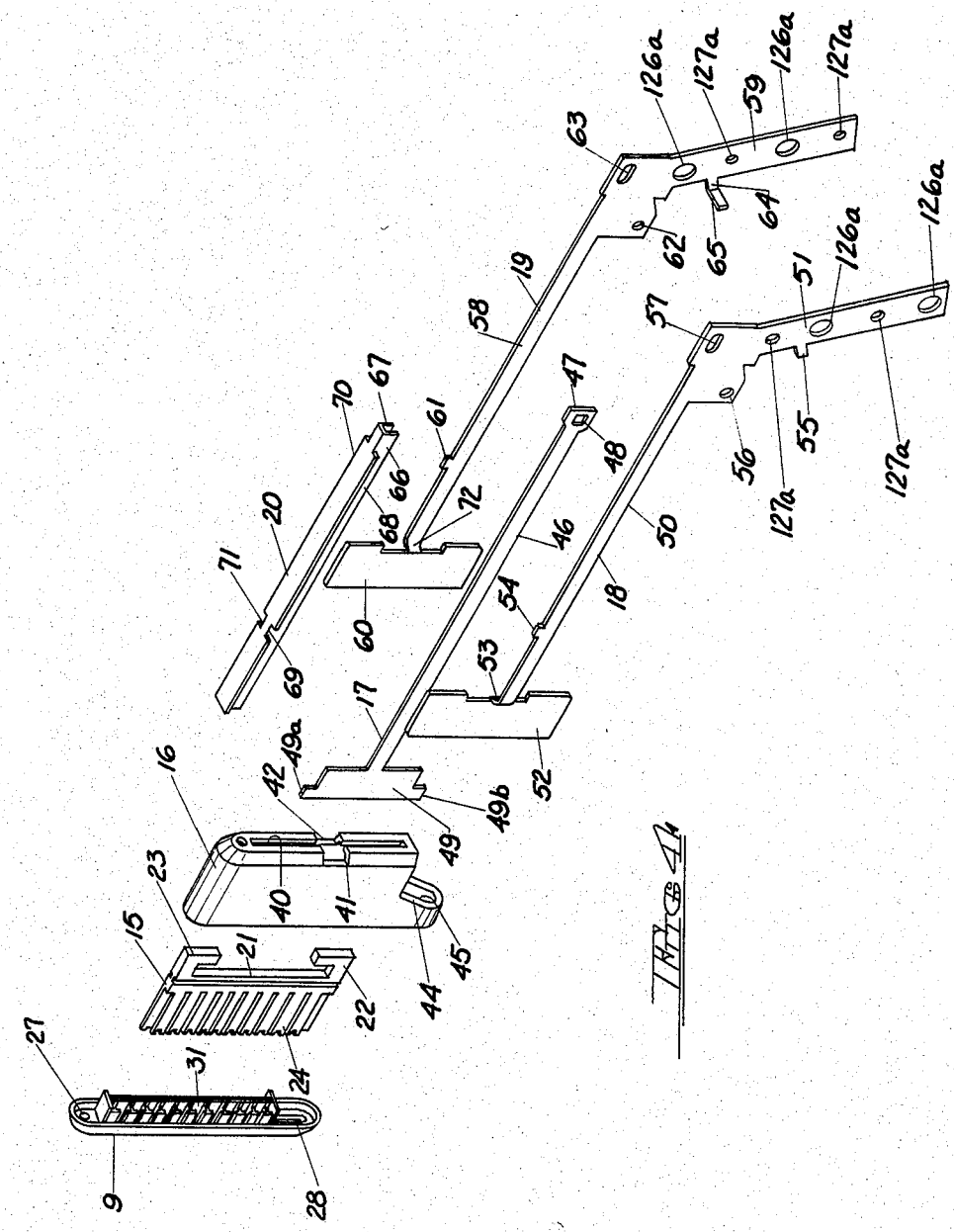

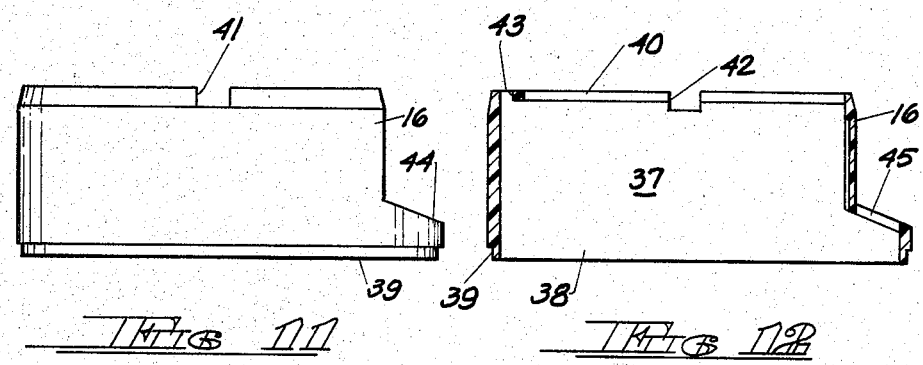
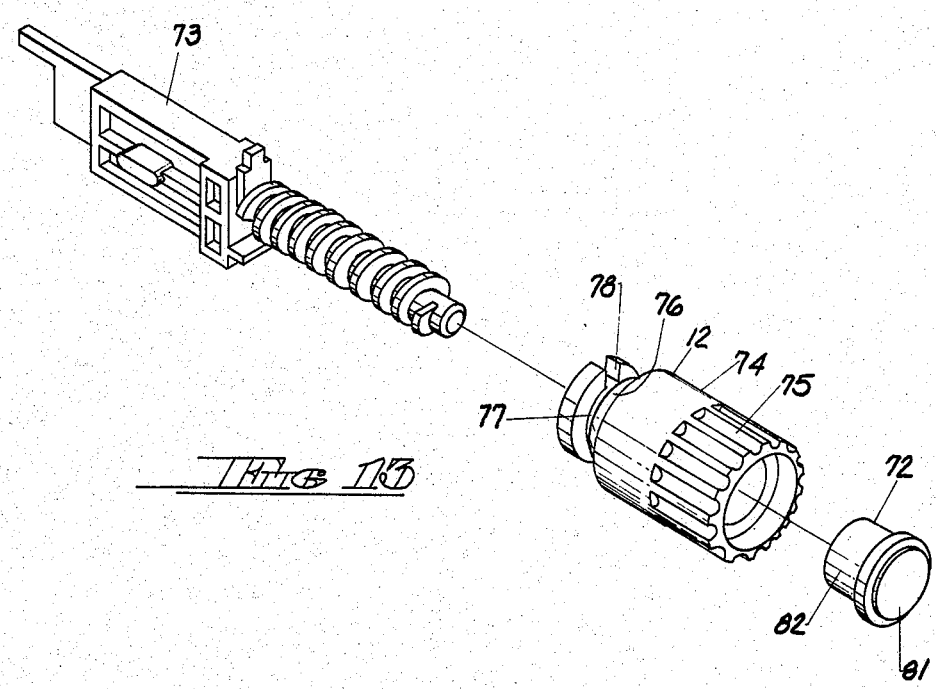

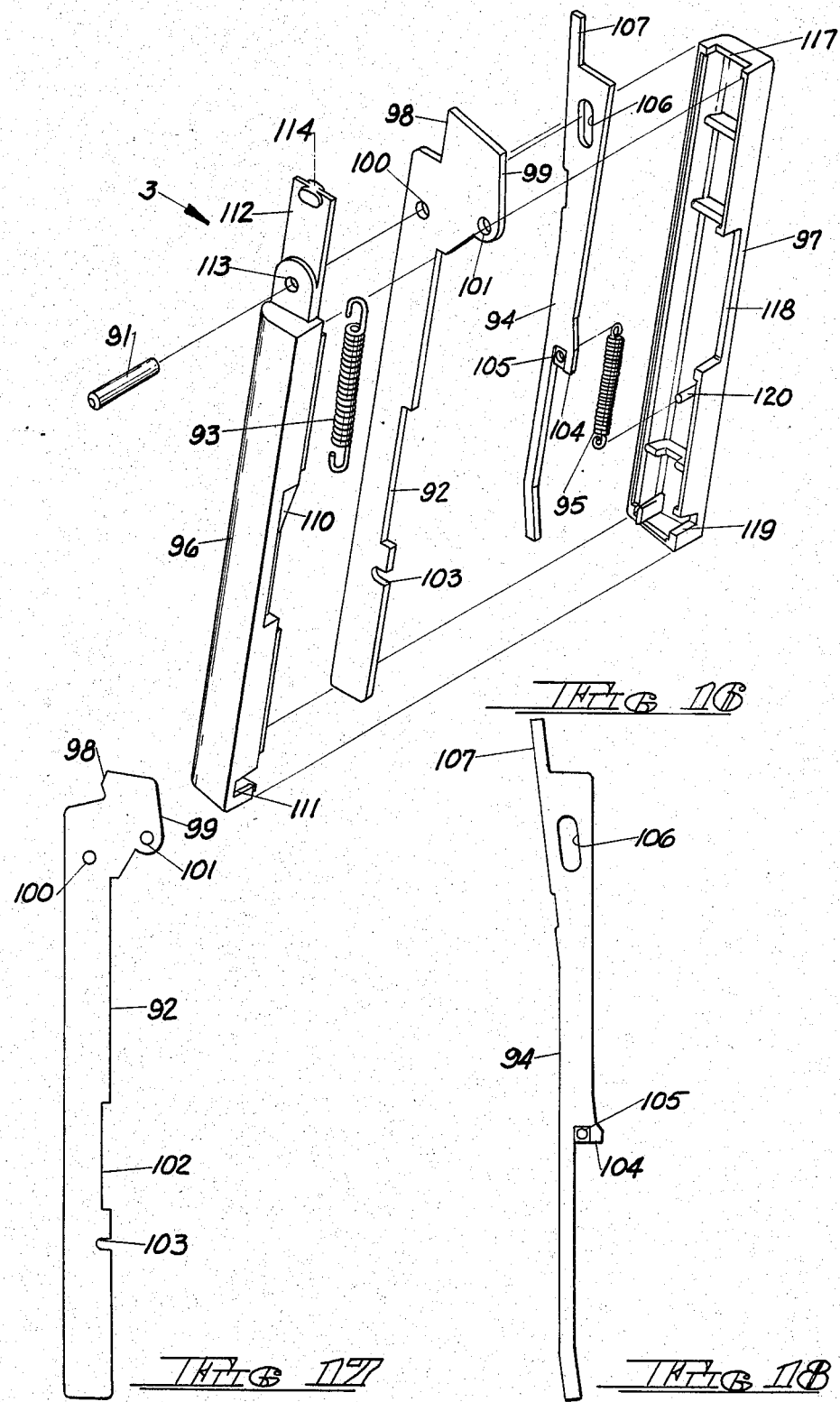

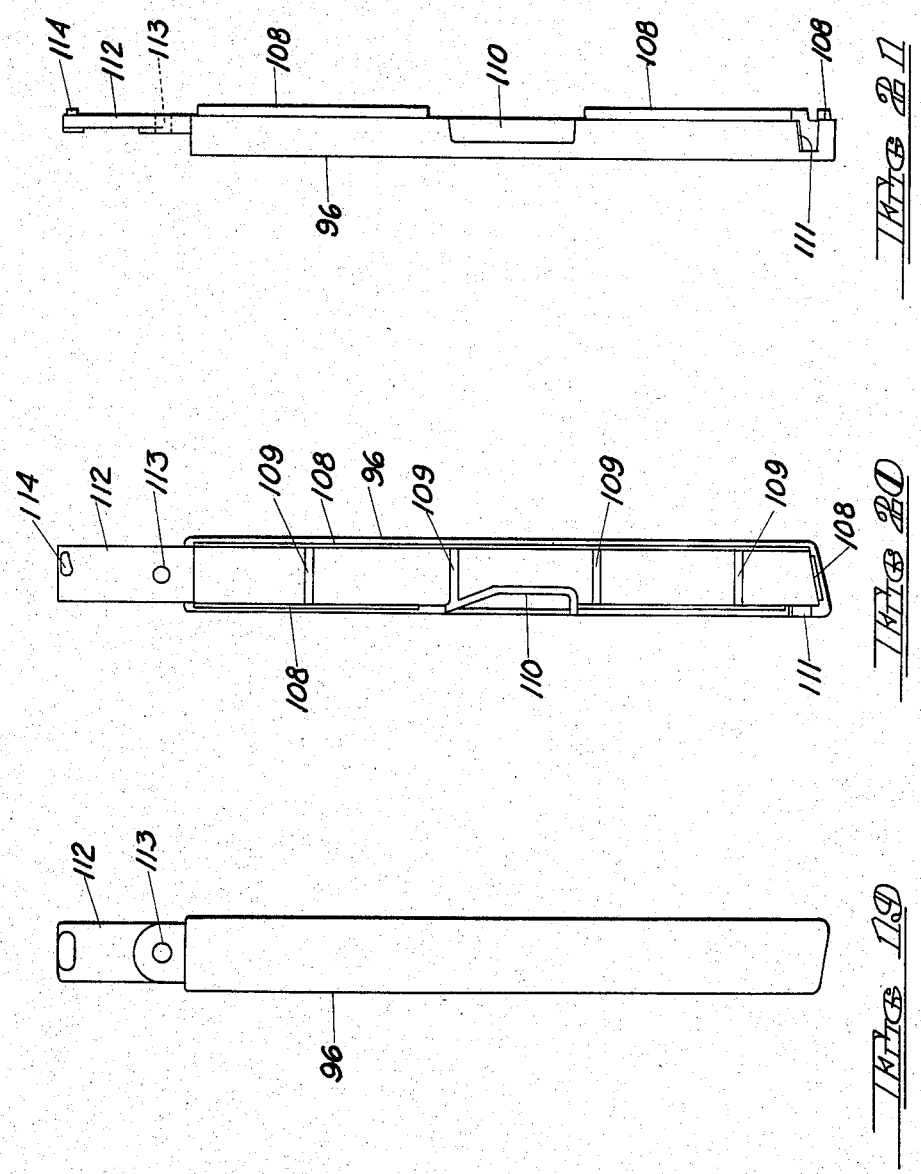

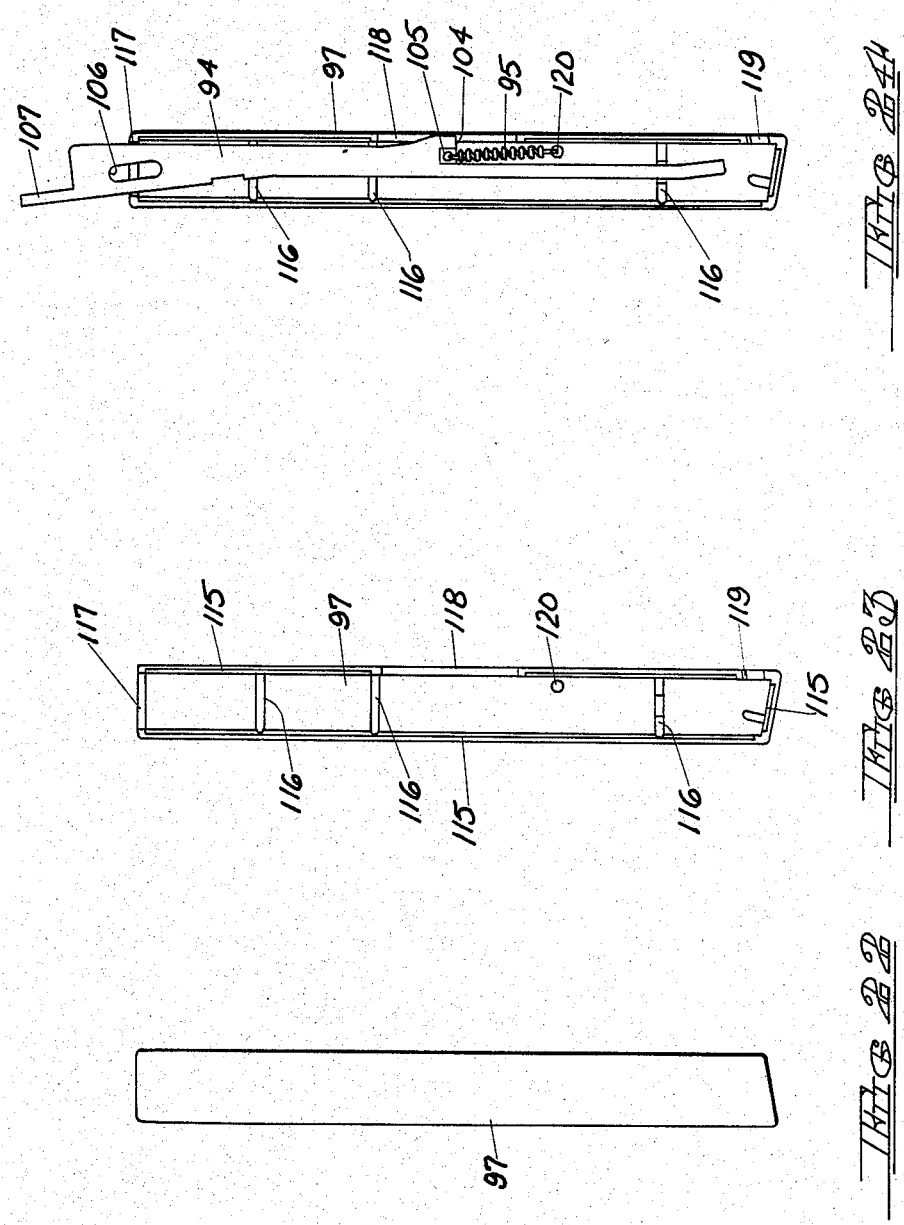

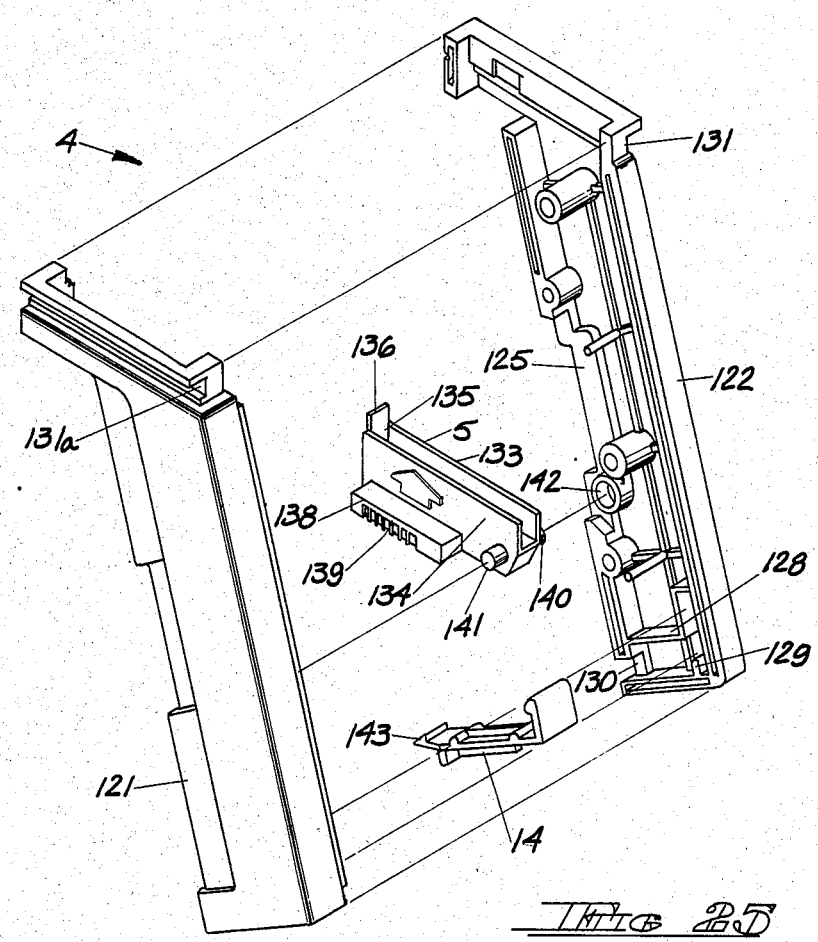
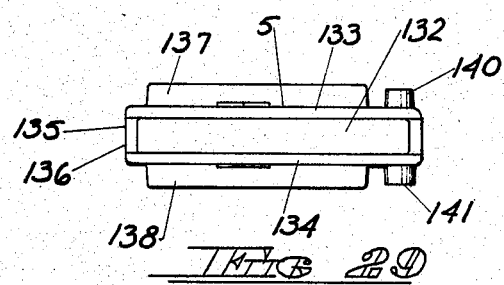

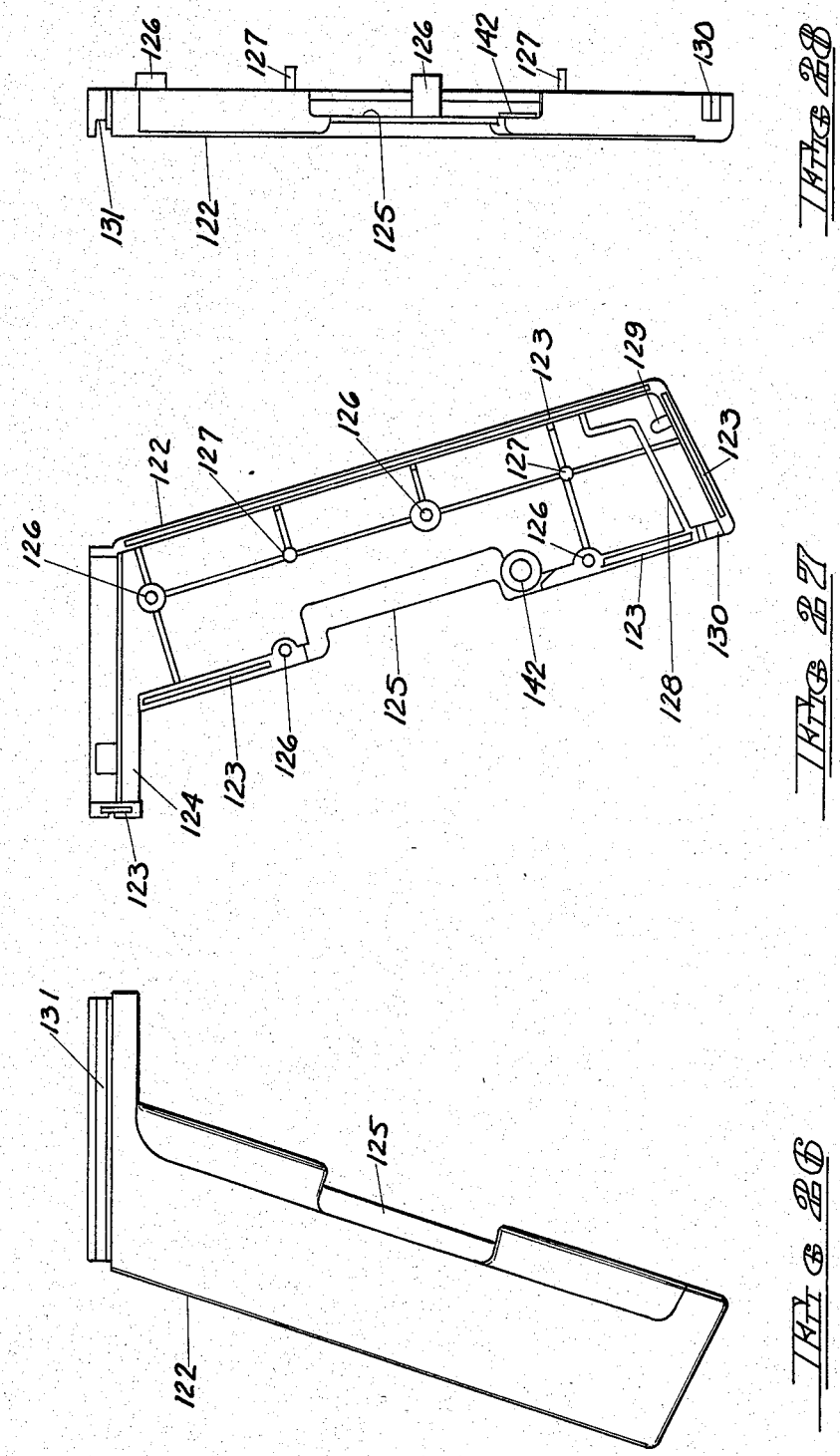

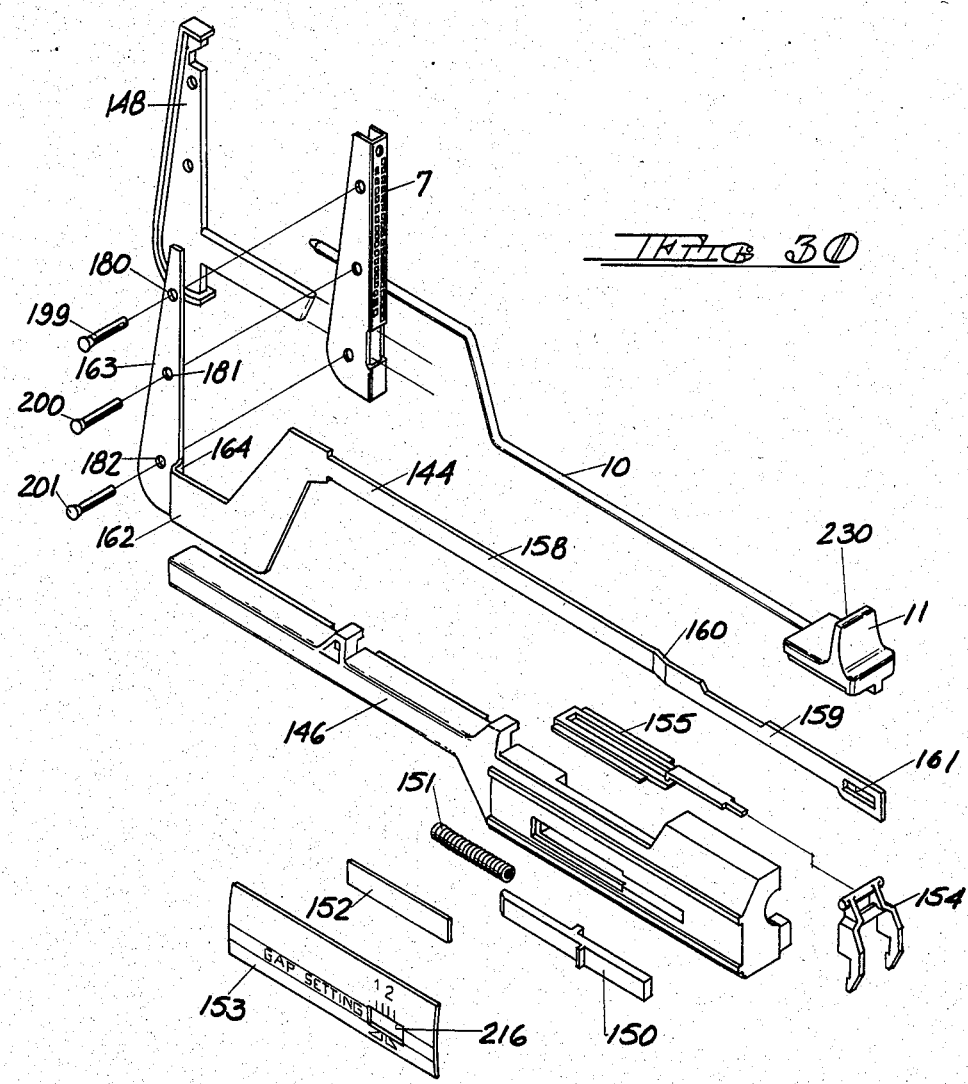

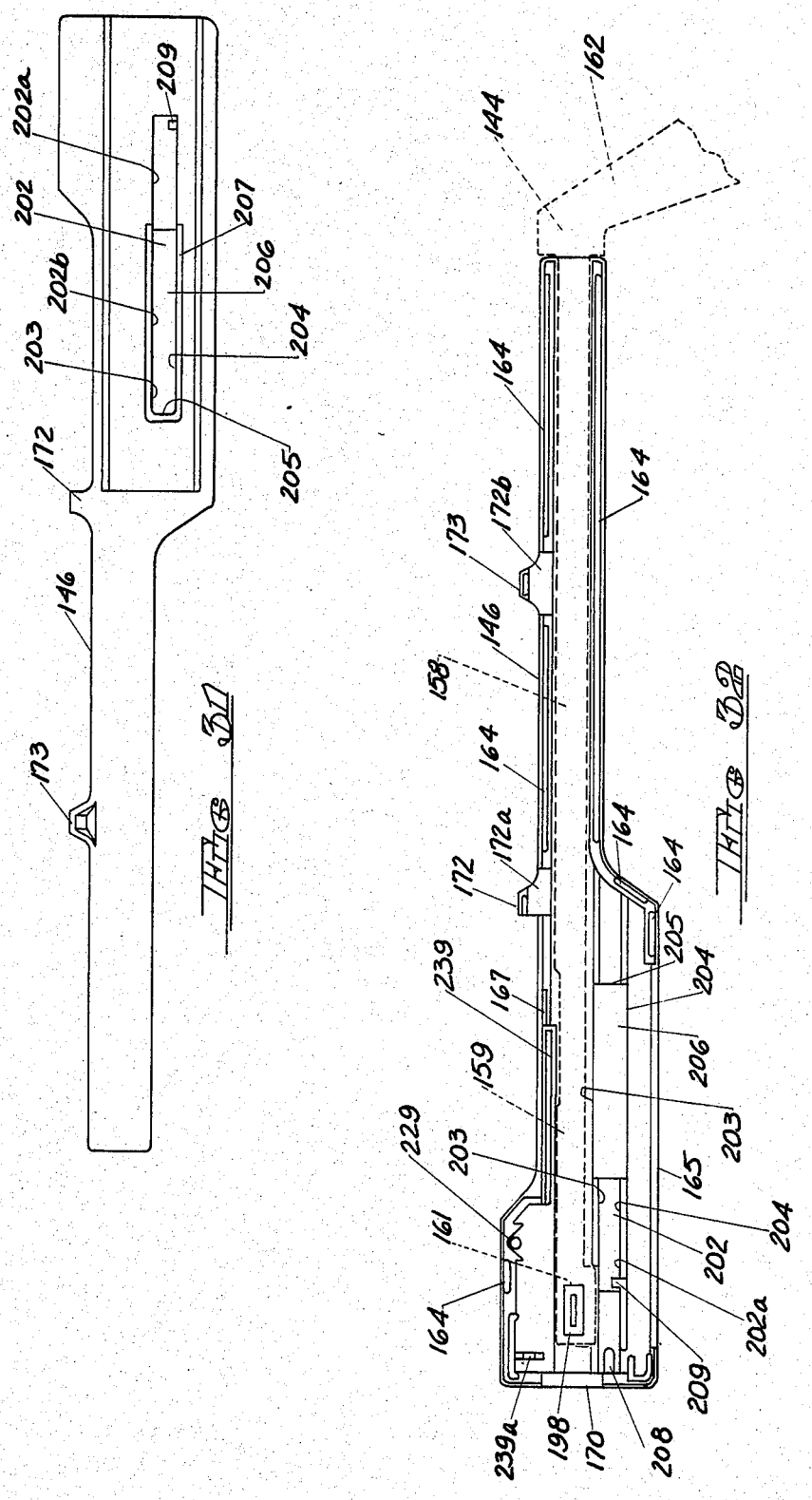

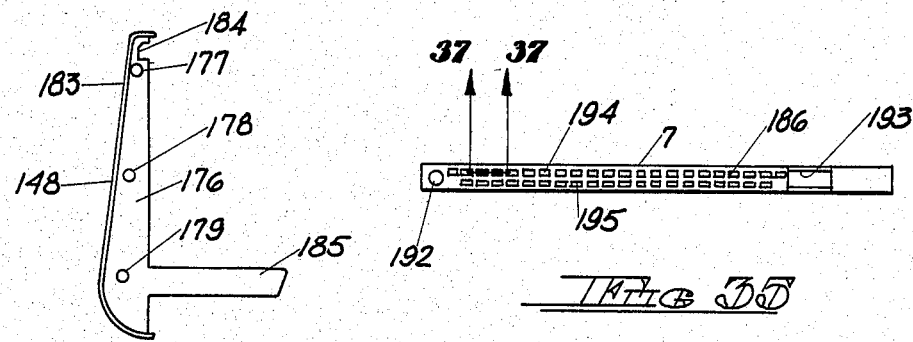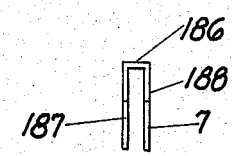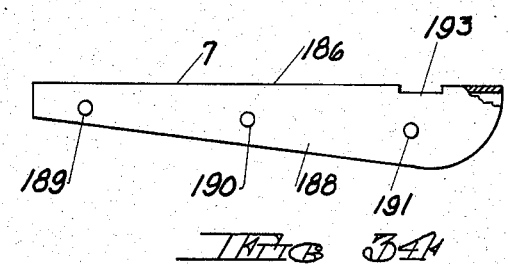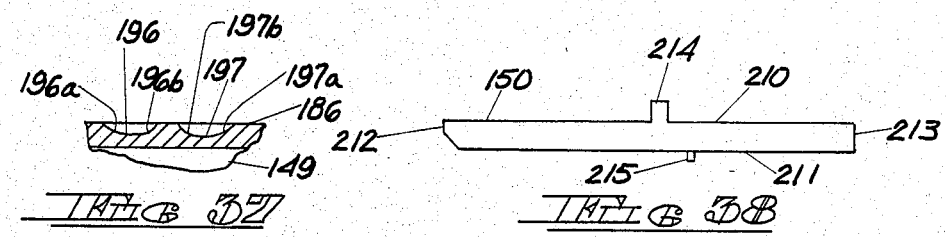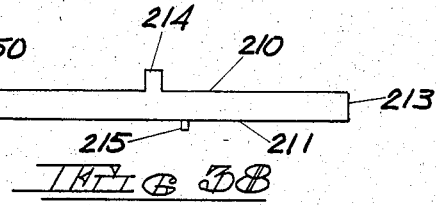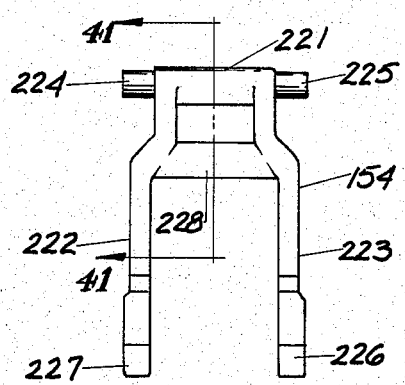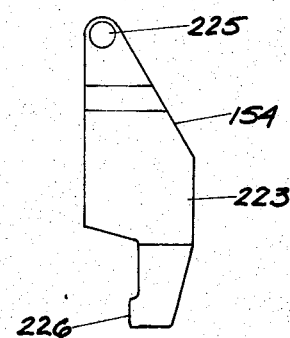

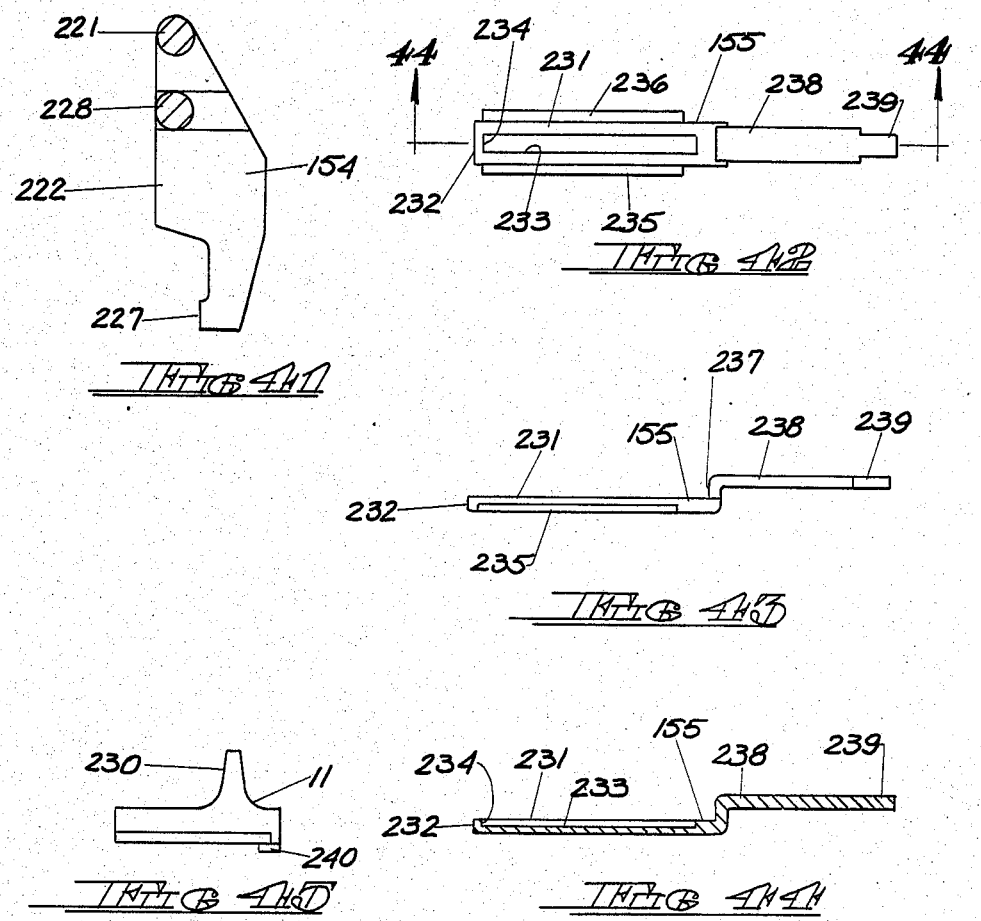

4,527,724

DISPOSABLE LINEAR SURGICAL STAPLING INSTRUMENT

TECHNICAL FIELD

The invention relates to a disposable linear surgical stapling instrument for forming and implanting at least one rectilinear row of surgical staples in the tissue of a patient, and more particularly to such an instrument having a working gap for use with a single size of surgical staple together with novel safety means which greatly reduce the opportunity for inadvertent or incorrect operation of the instrument.

BACKGROUND ART

In recent years there has been an increasing number of surgeons using surgical staples, rather than conventional sutures. This is true because the use of surgical staples and surgical stapling instruments has made many difficult procedures much simpler. Of even more importance, however, is the fact that the use of surgical staples significantly reduces the time required for most procedures, and therefore reduces the length of time for which the patient must be maintained under anesthetic. Many types of surgical stapling instruments have been devised, for many different procedures. The present invention is directed to a linear surgical stapling instrument. This is an instrument which, in a single actuation, implants and forms at least one rectilinear row of surgical staples. Such instruments are used on many different organs and tissues such as the lung, the esophagus, the stomach, the duodenum and throughout the intestinal tract.

In its earliest form, the linear surgical stapling instrument was a permanent, multi-use instrument and the surgical staples were manually loaded into the instrument one-by-one. An exemplary surgical stapling instrument of this type is taught in U.S. Pat. No. 3,080,564. While such instruments performed well, they were in general complex in construction, expensive to manufacture, heavy, bulky and difficult both to load with surgical staples and to clean and sterilize after each use.

The next significant improvement in linear surgical stapling instruments was the provision of presterilized, disposable loading units or staple cartridges. U.S. Pat. No. 3,275,211 and U.S. Pat. No. 3,589,589 are exemplary of those relating to permanent, multi-use linear instruments having replaceable staple cartridges. While this improvement significantly reduced the time previously required for hand loading of the staples, the basic instrument still had to be disassembled, cleaned, reassembled and sterilized for each procedure. Such instruments also frequently required maintenance and adjustment.

Even more recently, in view of rising hospital costs, there has been an ever increasing interest in disposable surgical stapling instruments to eliminate as much work as possible (i.e. disassembly, cleaning, reassembly, sterilization and the like) and to be more efficient, while at the same time not having to compromise the surgical procedures. U.S. Pat. No. 4,354,628 and U.S. Pat. No. 4,383,634, for example, each teach a disposable linear surgical stapling instrument. While devices of this sort perform well, since the forwardmost, anvil-carrying jaw is pivoted, the anvil and the cartridge do not approach each other in parallel relationship and only a single gap setting is achievable. In addition, it is sometimes difficult to properly position the tissue to be sutured within the jaws of an instrument of this design. Such instruments are frequently provided in a "tight" suturing version with short legged staples and a "loose" suturing version with staples having longer legs, the surgeon having to select the appropriate instrument for the particular procedure being performed.

The present invention provides a disposable linear surgical stapling instrument which is simple in construction and relatively inexpensive to manufacture. The instrument is characterized by a working gap or range of distances between the anvil and the cartridge over which a single size staple can be properly implanted and formed. The proper and desired setting of the instrument, within the working gap, is easily accomplished through simple manipulation of an adjustment knob at the rear of the instrument with indicator means on each side of the instrument to clearly show when the distance between the anvil and the cartridge is within the working gap. In addition, the gap to which the instrument is set can fall anywhere within the confines of the working gap of the instrument. The gap indicator is additionally designed to show at a glance whether the selected gap falls within the prior art so-called "tight" range or "loose" range.

In addition to many novel features of its own, the instrument of the present invention is also provided with features normally associated with permanent, multi-use instruments only. The instrument, for example, has an alignment and retaining pin, shiftable to an operative position wherein perfect alignment between the anvil and the staple cartridge is assured, and wherein tissue to be sutured and located between these elements is maintained therebetween. The instrument is provided with a locknut device which precludes rotation of the adjustment knob to secure the desired gap unless the alignment and retaining pin has been shifted to its operative position. The instrument is also provided with a novel trigger safety which will disable the trigger until the movable jaw of the instrument has been shifted to a position near the working gap. Latch means is also provided for the trigger, to secure the trigger with a snap engagement when the trigger is shifted to its fully actuated position, to give the surgeon a visual, tactile and audible indication that the surgical staples have been properly and fully implanted and formed. For purposes of economy and simplicity, much of the instrument is made of appropriate plastic material, while all of the major load-bearing elements of the instrument are metallic. The instrument is so designed that the staple driver is coupled to the trigger at all times. As a result of this, the driver is not free floating and cannot accidentally dislodge or discharge the surgical staples during shipping and handling prior to use of the instrument in the operating room.

DISCLOSURE OF THE INVENTION

According to the invention there is provided a disposable linear surgical stapling instument for forming and implanting at least one rectilinear row of surgical staples in the tissue of a patient. The instrument comprises a body having a handle and trigger assembly and being provided at its forward end with a fixed anvil-supporting jaw. The instrument also has a movable jaw comprising a staple cartridge. The movable jaw is mounted on the body and is operatively connected to the handle and trigger assembly.

An adjustment bolt is slidably mounted within the body and is shiftable forwardly and rearwardly therein. An adjustment knob is rotatably mounted at the rearward end of the body. The adjustment knob is operatively connected to the bolt to cause the bolt to shift forwardly and rearwardly.

When the adjustment bolt is shifted forwardly within the instrument body by means of the adjustment knob, the bolt moves the handle and trigger assembly forwardly and causes the movable jaw to approach the fixed jaw with the staple cartridge approaching the anvil. A staple driver is located in association with the cartridge and is connected to and shiftable by the trigger to drive staples from the cartridge, through the tissue to be sutured (located between the cartridge and the anvil), and against the anvil. The anvil has a plurality of anvil pockets configured to clinch the staples over a range of distances between the anvil and the cartridge, constituting the working gap of the instrument. The adjustment bolt also actuates indicator means to each side of the instrument, clearly showing when the working gap has been achieved between the anvil and the cartridge. The indicator is such that it will assist the surgeon in adjusting the distance between the anvil and the cartridge within the working gap.

An alignment pin is shiftably mounted on the instrument body, extending through the cartridge. The alignment pin is manually shiftable to an operative position wherein it also extends into the fixed jaw. In this way, the alignment pin not only assures that the anvil and the cartridge are properly oriented with respect to each other, but also traps the tissue to be sutured between the anvil and the cartridge.

A safety lockout is provided which precludes rotation of the adjustment knob unless and until the alignment and retaining pin has been shifted to its operative position. A second safety locknut disables the trigger unless and until the distance between the anvil and cartridge approaches the working gap of the instrument.

A lock is also provided in association with the handle to engage and lock the trigger when the handle reaches its full actuated position. This gives the surgeon a visual, audible and tactile indication that the surgical staples have been fully implanted and formed.

BRIEF DESCRIPTION OF THE DRAWINGS

FIG. 1 is a side elevational view of the linear surgical stapling instrument of the present invention.

FIG. 2 is a plan view of the instrument of FIG. 1.

FIG. 3 is a cross-sectional elevational view, taken along section line 3—3 of FIG. 2.

FIG. 4 is an exploded perspective view of the movable jaw or cartridge/driver subassembly of the present invention.

FIG. 5 is an elevational view of the driver of the present invention.

FIG. 6 is a plan view of the driver of FIG. 5.

FIG. 11 is elevational view of the casing of the present invention.

FIG. 12 is a cross-sectional elevational view of the casing of FIG. 11.

FIG. 13 is an exploded perspective view of the adjustment bolt/adjustment knob subassembly of the present invention.

FIG. 16 is an exploded perspective view of the trigger subassembly of the present invention.

FIG. 17 is an elevational view of the trigger.

FIG. 18 is an elevational view of the safety lockout of the trigger subassembly.

FIGS. 19, 20 and 21 are, respectively, outside elevational, inside elevational and rear views of the left trigger cover.

FIGS. 22 and 23 are, respectively, outside elevational and inside elevational views of the right trigger cover.

FIG. 24 is an elevational view of the right trigger cover illustrating the safety lockout and lockout spring mounted therein.

FIG. 25 is an exploded perspective view of the handle subassembly of the present invention.

FIGS. 26, 27 and 28 are, respectively, an outside elevational view, an inside elevational view and a front elevational view of the right handle half.

FIG. 29 is a plan view of the trigger safety.

FIG. 30 is an exploded perspective partial view of the body/hook/pilot/anvil/indicator/alignment and retaining pin subassembly of the present invention.

FIG. 31 is an outside elevational view of the left body half.

FIG. 32 is an inside elevational view of the left body half.

FIG. 33 is an elevational view of the pilot.

FIGS. 34, 35 and 36 constitute, respectively, a side elevational view, a plan view and an end elevational view of the anvil.

FIG. 37 is a fragmentary cross sectional view of the anvil taken along section line 37—37 of FIG. 35.

FIG. 38 is an edge elevational view of the indicator slide.

FIGS. 39 and 40 are, respectively, a side elevational view and a front elevational view of the slide crank.

FIG. 41 is a cross-sectional view of the slide crank taken along section line 41—41 of FIG. 40.

FIGS. 42 and 43 are respectively a plan view and a side elevational view of the knob lockout.

FIG. 44 is a cross-sectional view of the knob lockout taken along section line 44—44 of FIG. 42.

FIG. 45 is a side elevational view of the alignment and retaining pin knob.

DETAILED DESCRIPTION OF THE INVENTION

Figure 7:
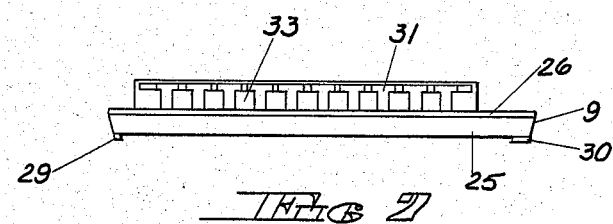
FIGS. 7, 8 and 9 are respectively, an elevational view, a rear view and a front view of the cartridge of the present invention.
Figure 8:
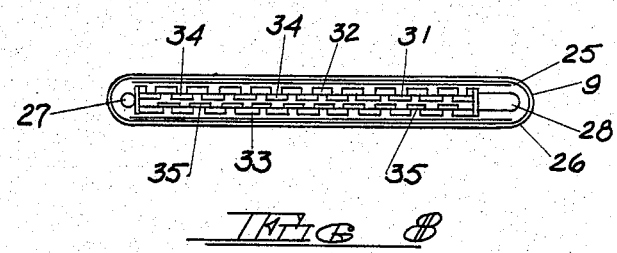
Figure 9:
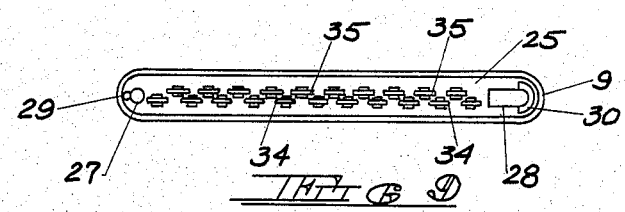

For convenience and ease of understanding, like parts have been given like index numerals in all of the Figures. Reference is first made to FIGS. 1 and 2. These Figures are, respectively, a side elevational view and a plan view of the instrument of the present invention. The instrument is generally indicated at 1 and comprises a body 2. The body 2 has a trigger subassembly generally indicated at 3 and a handle subassembly generally indicated at 4. A trigger safety is shown at 5.

At its forward end, the instrument terminates in a fixed jaw generally indicated at 6 supporting an anvil 7. The instrument is also provided with a movable jaw (generally indicated at 8) which comprises, in part, a cartridge 9 for surgical staples. The upper portion of body 2 supports an alignment and retaining pin 10. The alignment and retaining pin 10 extends through movable jaw 8. The pin is manually shiftable by means of knob 11 forwardly to a position wherein it also extends into the anvil 7 and fixed jaw 6 to assure that the anvil 7 is properly aligned with the cartridge 9.

At its rearward end, the instrument is provided with an adjustment knob 12, the purpose of which will be apparent hereinafter. On each of its sides, the instrument is provided with a gap setting indicator. One of the indicators is generally shown at 13 in FIG. 1. The handle assembly 4 is provided with a handle snap lock 14, the purpose of which will be described hereinafter.

From this point forward, the various parts of the instrument of the present invention will be described in groups or subassemblies for purposes of clarity and ease of understanding. While reference will be made to specific Figures, reference should also be made to FIGS. 1 through 3 which show the instrument in fully assembled condition.

Reference is first made to FIG. 4 wherein movable jaw or the cartridge/driver subassembly is illustrated in an exploded view. This subassembly comprises the cartridge 9, a staple driver 15, a casing 16, a driver rod 17, a left handle plate 18, a right handle plate 19 and a spacer 20.

Driver 15, which is molded of an appropriate plastic material, is best shown in FIGS. 5 and 6. Like all of the other plastic parts to be described, driver 15 is formed of a plastic material of adequate strength, suitable for use in a surgical environment, and capable of sterilization by one or more of the known and well accepted methods. Such plastic materials are well known in the art.

The driver 15 is an integral, one-piece element comprising an elongated body 21 having, at its ends, rearwardly extending hook-like elements 22 and 23. The driver 15 is provided with a plurality of forwardly extending tines 24. The tines 24 are equal in number to the number of staples housed in cartridge 9. As can most clearly be seen in FIG. 6, the forwardly extending tines 24 are arranged in two parallel, spaced rows, with the tines of one row staggered with respect to the tines of the other.

The cartridge 9 is best shown in FIGS. 7 through 10. The cartridge 9 constitutes an integral, one-piece molded plastic member comprising an elongated body 25 having an upstanding surrounding flange 26. At one end, the body 25 has a circular perforation 27, and at the other end it is provided with an elongated slot 28. The purpose of perforation 27 and slot 28 will be apparent hereinafter.

The forward surface of cartridge 9 (i.e., that surface which will face the anvil), is provided with a forwardly extending spacer element 29 adjacent perforation 27 and a forwardly extending spacer 30 adjacent the outermost end of slot 28. These spacers 29 and 30 are most clearly shown in FIGS. 7 and 9. These spacers cooperate with the anvil (to be described hereinafter) to determine the forwardmost position of cartridge 9.

The cartridge 9 is provided with a centrally located, longitudinally extending, wall 31, flanked to either side by segmented walls 32 and 33. These walls 31, 32 and 33 define two parallel rows of staggered pockets or slots 34 and 35. The pockets or slots 34 and 35 extend through the forward face of cartridge 9, as is most clearly shown in FIGS. 9 and 10.

Each slot 34 is provided at its ends with additional grooves 34a and 34b intended to frictionally receive the legs of a surgical staple. Each slot 35 is provided with similar additional grooves 35a and 35b, serving the same purpose. In this way, a surgical staple can be loaded in each of slots 34 and 35.

Reference is now made to FIG. 3. As is shown in FIG. 3, the tines 24 of driver 15 are insertable within the slots 34 and 35 of cartridge 9. FIG. 3 illustrates a surgical staple 36 located within one of the slots 35. It will be noted that the corresponding driver tine 24 overlies the crown of the staple. It will be apparent from this that when the driver 15 is shifted forwardly relative to cartridge 9, the surgical staple 36 will be shoved forwardly out of its slot 35. The driver 15 will similarly shove all of the surgical staples from their respective cartridge slots.

The cartridge casing 16 is illustrated in FIGS. 11 and 12. The casing 16, like driver 15 and cartridge 9, is an integral, one-piece, molded plastic member. The casing 16 is hollow, defining a chamber 37. The forward end of the casing is open, as at 38, and is surrounded by a flange 39. The flange 39 is so sized as to just nicely fit within the flange 26 of cartridge 9 and the casing 16 and cartridge 9 are joined together thereby through the use of ultrasonic welding, gluing or the like. The rearward end of casing 16 is provided with an elongated, longitudinally extending slot 40, the purpose of which will be apparent hereinafter. The side walls of casing 16, centrally of slot 40, are notched as at 41 and 42. Again, the purpose of these notches will be apparent hereinafter. Finally, the rearward end of casing 16 is provided with a perforation 43 coaxial with the perforation 27 of cartridge 9. The lower edge of casing 16 is stepped inwardly, as at 44 and the inwardly stepped portion 44 is provided with an elongated slot 45, corresponding to elongated slot 28 of cartridge 9. FIG. 3 illustrates the assembly of casing 16 and cartridge 9. It will be noted that driver 15 is shiftably mounted within casing 16.

Reference is now made to FIG. 4. The driver rod 17 comprises a metallic member having an elongated shank 46. At its rearward end, the elongated shank is enlarged as at 47 and provided with a transverse opening or perforation 48. At its forward end, the shank 46 terminates in a plate-like structure 49 having upper and lower lugs 49a and 49b near its forwardmost end. As can be readily seen in FIG. 3, the plate-like forward end 49 of driver rod 17 is located within casing 16 with its lugs 49a and 49b just nicely received within the hook-like portions 23 and 22, respectively, of driver 15. The forwardmost end of the driver rod plate-like structure 49 abuts the elongated body portion 21 of driver 15. Thus, the forward end of the driver rod 17 is locked into engagement with the driver 15 and when the driver rod 17 is shifted in a forward direction, it will shift the driver 15 forwardly as well.

FIG. 4 illustrates the left handle plate 18 and right handle plate 19. These elements constitute the "main frame" of the surgical stapling instrument and are made of metal. The left handle plate 18 comprises an elongated shank-like portion 50, terminating at one end in a handle portion 51 and at the other end in a plate-like structure 52. The shank portion 50 and handle portion 51 are coplanar. The forward plate-like portion 52 is parallel to portions 50 and 51 but is slightly inset with respect thereto as at 53. The shank-like portion 50 has an upstanding lug 54, the purpose of which will be apparent hereinafter. The handle portion 51 has a forwardly extending lug 55 for purposes to be described. It is also provided with a perforation 56 to serve as a bearing for the pivot pin of the trigger assembly and an elongated slot 57 adapted to cooperate with the adjustment bolt of the instrument.

The right handle plate 19 is a mirror image of the left handle plate 18 and consequently has a shank portion 58, a handle portion 59 and a slightly offset plate-like portion 60. The shank portion 58 is provided with a lug 61 corresponding to lug 54. The handle portion 59 is provided with a perforation 62 corresponding to perforation 56 of left handle plate 18 and also serving as a bearing for the trigger assembly pivot pin. The handle portion 59 has an elongated slot 63 corresponding to elongated slot 57 of handle portion 51 and intended to cooperate with the adjustment bolt, as will be described. Handle portion 59 also has a forwardly extending lug 64, corresponding to lug 55 of handle portion 51. The only difference between the right handle plate 19 and the left handle plate 18 lies in the fact that the forwardly extending lug 64 has a transverse extension 65 formed thereon, the purpose of which will be described.

To complete this subassembly illustrated in FIG. 4, a spacer 20 is provided. The spacer 20 is molded of plastic material and, as can be clearly seen in FIG. 4, is of channel-shaped cross section having a pair of downwardly depending leg portions 66 and 67. The spacer 20 is also provided on one side with a laterally extending flange 68 with a notch 69 therein. A similar flange 70 is provided on the other side of the spacer 20, having a notch 71 formed therein. Referring to both FIGS. 3 and 4, the forward plate-like structures 52 and 60 of handle plates 18 and 19 are located within casing 16, to either side of the plate-like portion 49 of driver rod 17. The offset portion 53 of left handle plate 18 is accommodated by the notch 41 of casing 16. Similarly, the corresponding offset portion 72 of right handle plate 19 is accommodated by notch 42 of casing 16.

The elongated shank portion 46 of driver rod 17 is located between the downwardly depending legs 66 and 67 of spacer 20. The elongated shank 50 of left handle plate 18 lies along the outside of downwardly depending leg 66 of spacer 20, while the elongated shank 58 of right handle plate 19 lies along the outside surface of downwardly depending spacer leg 67. In this way, the elongated shanks 50 and 58 of handle plates 18 and 19 are separated from each other and from the elongated shank 46 of driver rod 17. To maintain spacer 20 in proper position with respect to these elements, the upstanding lug 54 on the shank 50 of left handle plate 18 is received within the notch 69 of spacer 20 while the upstanding lug 61 of the shank 58 of right handle plate 19 is received within notch 71 of spacer 20.

FIG. 13 is an exploded view illustrating the adjustment bolt/adjustment knob subassembly of the present invention. This subassembly comprises the adjustment knob 12, the adjustment knob end cap 72 and the adjustment bolt 73.

The adjustment knob 12 and its end cap 72 are most clearly illustrated in FIGS. 3 and 13. The adjustment knob 12 comprises a cylindrical molded plastic member having a main body portion 74, the rearward portion of which may be fluted or the like as at 75 to enable it to be readily grasped manually for rotation. The forward portion 76 of the adjustment knob 12 is of lesser diameter and is provided with an annular notch 77. The forwardmost part of knob portion 76 is provided with a transverse notch 78.

The main body portion 74 of knob 12 is hollow, having a central bore 79. The lesser diameter portion 76 of knob 12 also has a central bore 80, which is internally threaded.

End cap 72 comprises a molded plastic member have a circular body portion 81 with a forwardly extending, annular, cylindrical skirt 82. The skirt 82 is adapted to be received within the bore 79 of the adjustment knob main body portion 74 with a frictional fit, as shown in FIG. 3.

The adjustment bolt 73 of this subassembly is illustrated in FIGS. 3, 13, 14 and 15. The adjustment bolt 73 constitutes a molded plastic member comprising a main body portion 83 terminating at its forward end in a planar extension 84 having a forwardly directed coplanar finger 85. The planar extension 84 and finger 85 serve as spacer elements for the trigger assembly, as will be described hereinafter. The main body portion 83 of bolt 73 has a pair of opposed, laterally extending lugs 86 and 87. The lug 87 is adapted to be received in the elongated slot 57 of the handle portion 51 of the left handle plate 18, while the lug 86 is adapted to be received in the elongated slot 63 of the handle portion 59 of the right handle plate 19.

Extending rearwardly of its main body portion 83, the adjustment bolt 73 has a threaded shaft 88 adapted to be threadedly engaged in the threaded bore 80 of adjustment knob 12, as shown in FIG. 3. The threads of adjustment bolt shaft 88 and adjustment knob bore 80 are so arranged that when the adjustment knob 12 is manually rotated in a clockwise direction, the adjustment bolt 73 will shift forwardly with respect thereto.

To complete adjustment bolt 73, its main body portion 83 has a rearwardly extending lug 89 and a rearwardly and upwardly extending lug 90. The lugs 89 and 90 serve as abutment stops for adjustment knob 12 and adjustment bolt 73. The rearwardly and upwardly extending lug 90 serves as an actuating means for the indicator slide crank, as will be described hereinafter.

The trigger subassembly 3 of the present invention is illustrated in FIG. 16. The trigger subassembly 3 comprises trigger pivot pin 91, trigger 92, trigger spring 93, trigger lockout 94, trigger lockout spring 95, left trigger cover 96 and right trigger cover 97.

Trigger 92 is an elongated, planar, metallic member having a somewhat enlarged upper end, as is shown in FIG. 17. The upper end has a forwardly facing surface 98 adapted to contact the enlarged rearward end 47 of driver rod 17. The upper end of trigger 92 has a second edge 99 adapted to engage the forward end 83a of the main body portion 83 of the adjustment bolt 73 to determine the unactuated position of the trigger assembly. The engagement of the enlarged rearward end 47 of driver rod 17 by trigger edge 98 and the engagement of trigger edge 99 by the forward surface 83a of adjustment bolt 73 are illustrated in FIG. 3.

The upper end of trigger 92 is provided with a perforation 100 adapted to receive trigger pivot pin 91. It is also provided with a second perforation 101 adapted to receive the hooked upper end of trigger spring 93. Trigger spring 93 is intended to bias the trigger assembly 3 to its non-actuated position, as will be described hereinafter. To complete trigger 92, its rearward edge is provided with an elongated notch 102 giving clearance for trigger safety 5, as will be apparent hereinafter, and a second notch 103 providing clearance for a spring mount in the right trigger cover 97, again as will be apparent hereinafter.

The trigger safety lockout 94 is illustrated in FIGS. 16 and 18. Trigger safety lockout 94 comprises an elongated plastic member having, about midway of its length, an abutment surface 104 to be engaged by trigger safety 5. Adjacent abutment surface 104, the trigger safety lockout 94 is provided with a perforation 105 adapted to receive the upper hook-shaped end of trigger safety lockout spring 95. Near its upper end, the trigger safety lockout 94 has an elongated perforation or slot 106 through which trigger pivot pin 91 extends. Finally, at its uppermost end, the trigger safety lockout 94 is provided with an upward extension 107, the purpose of which will be described hereinafter.

The left trigger cover 96 is illustrated in FIG. 16 and in FIGS. 19, 20 and 21 as well. FIG. 19 is an outside elevational view of the left trigger half 96, while FIG. 20 is an inside elevational view thereof and FIG. 21 is a rear elevational view thereof. The trigger half 96 is an essentially hollow elongated plastic member having joinder flanges 108 along its forward, rearward and bottom edges. The left trigger cover also has a plurality of reinforcing ribs 109 extending transversely thereof. Its rearward edge is provided with a depression 110 to provide clearance for the trigger safety 5. The rearward edge of the left trigger cover 96 is also provided with a slot 111, the purpose of which will be apparent hereinafter.

At its upper end, the left trigger cover 96 is provided with an integral extension 112 having a perforation 113 extending transversely therethrough. As is apparent from FIG. 16, the perforation 113 is adapted to receive the trigger pivot pin 91. Finally, on its inside surface, the upward extension 112 is provided with a lug 114. Lug 114 is adapted to be received within the opening 48 in the enlarged end 47 of driver rod 17. In this way, the driver rod 17 and drive 15 are operatively connected, at all times, to trigger assembly 3.

The right trigger cover 97 is illustrated in FIGS. 22 through 24. The right trigger cover 97 is very nearly a mirror image of the left trigger cover 96. The right trigger cover 97 has indentations 115 along its forward, rearward and bottom edges, adapted to receive the joinder flanges 108 of left trigger cover 96. The right trigger cover 97 also is provided with transversely extending reinforcing ribs 116, similar to the reinforcing ribs 109 of left trigger cover 96. The upper end of right trigger cover 97 is not provided with an extension equivalent to the extension 112 of left trigger cover 96. Rather, the upper end of right trigger cover 97 is provided with a notch 117 adapted to provide clearance for the upper portion of trigger safety lockout 94. In its rearward edge, the right trigger cover 97 has an elongated notch 118 to provide access to and clearance for the trigger safety lockout 94. It is also provided, near its lower end, with a second notch 119. The notch 119 cooperates with the corresponding notch 111 in left trigger half 96 to form a single continuous notch across the trigger assembly when the parts are joined together. To complete the structure, the inside surface of right trigger cover 97 is provided with a pin 120 which serves as an anchor for the lower end of the trigger safety lockout spring 95. FIG. 24, which is similar to FIG. 23, illustrates the trigger safety lockout 94 mounted in place within the right trigger cover 97. It will be noted that the trigger safety lockout spring 95 tends to urge the trigger safety lockout 94 downwardly with respect to the right trigger cover 97.

Referring to FIGS. 16 and 24, the trigger subassembly 3 is assembled by locating the trigger safety lockout 94 in the right trigger cover 97 with the upper end of trigger safety lockout spring 95 mounted in the trigger safety lockout perforation 105 and the lower end of spring 95 affixed to the anchor pin 120 of the right trigger cover 97. The metallic trigger 92 is located within this assembly and the left trigger half 96 is then affixed to the right trigger half 97 by locating the joinder flanges 108 of left trigger half 96 within the indentations 115 in the right trigger half 97 and joining these plastic elements together by ultrasonic welding, glue or the like. The trigger pivot pin 91 is then located within perforation 113 of the left trigger half 96, perforation 100 in the metallic trigger 92 and elongated slot 106 within trigger safety lockout 94.

Turning to FIG. 4, the free ends of the trigger pivot pin 91 pass through the perforation 56 of left handle plate 18 and the perforation 62 of right handle plate 19, the perforations 56 and 62 serving as bearings for the pivot pin 91. When this assembly is made, the free end of trigger spring 93 is hooked on the extension 65 of the lug 64 on handle portion 59 of right handle plate 19. With these parts assembled, the lug 55 of handle portion 51 of left handle plate 18 abuts the free end of the extension 65 on right handle plate 19, thus preventing the lower end of trigger spring 93 from slipping off the extension 65. The attachment of the free end of trigger spring 93 to the handle plate extension 65 is illustrated in FIG. 3.

It will also be apparent from FIGS. 3, 20 and 25 that the depression 110 in the rearward edge of the left trigger cover 96 and the notch 118 in the rearward edge of the right trigger cover 97 expose the operating abutment surface 104 of the trigger safety lockout 94 and provide clearance for engagement thereof by trigger safety 5, to be described hereinafter.

The handle subassembly 4 of the present invention is illustrated in FIG. 25. The handle subassembly 4 comprises a left handle half 121, a right handle half 122, trigger safety 5 and handle snap lock 14.

The right handle half 122 is illustrated in FIGS. 26, 27 and 28. Handle half 122 is a hollow plastic member, the front, bottom and rear edges of which are provided with elongated depressions 123 adapted to receive similarly placed flanges on left handle half 121, by which the handle halves 121 and 122 are joined together. Handle half 122 has an opening 124 adapted to accommodate the trigger assembly 3. In its forward edge, it also has an elongated notch 125 adapted to accept trigger safety 5, when in its retracted position. The right handle half 122 has a plurality of sockets 126 and a plurality of joinder pins 127. It will be understood that the left handle half 121 will have sockets equivalent to sockets 126 at the position of the pins 127 in right handle half 122 and will have pins equivalent to pins 127 at the positions of the sockets 126 in right handle half 122, by which the handle halves 121 and 122 are joined together. Sockets 126 in handle halves 121 and 122 pass through corresponding perforations 126a in handle portions 51 and 59 of handle plates 18 and 19, respectively; while pins 127 in handle halves 121 and 122 pass through corresponding perforations 127a in handle portions 51 and 59 of handle plates 18 and 19, respectively. This arrangement aids in positioning and alignment of parts upon assembly. The handle halves may be joined permanently by glue, ultrasonic welding, or the like. Near its bottom, the right handle half 122 has a web or wall 128 forming a socket for the handle snap lock 14. A second small wall 129 is provided as part of the snap lock socket. A notch 130 is located in the lower forward edge of handle half 122 to allow the free end of the handle snap lock 14 to extend beyond the confines of the handle half 122. Finally, the uppermost end of handle half 122 is provided with a longitudinal slot 131, the purpose of which will be evident hereinafter.

It will be understood that the left handle half 121 constitutes substantially a mirror image of the right handle half in all respects save the locations of the joinder pins 127 and sockets 126 and the fact that it is provided with flanges to be received in the depressions 123 of right handle half 122.

Trigger safety 5 is illustrated in FIGS. 25 and 29. Trigger safety 5 is a molded plastic member comprising a bottom wall 132, a pair of upstanding side walls 133 and 134 and a front end wall 135 with an extension 136 extending above the side walls 133 and 134. Flanges 137 and 138 extend laterally of side walls 133 and 134. The outside surface of bottom wall 132 and flanges 137 and 138 may be grooved as at 139 (see FIGS. 3 and 25) to afford better manual engagement thereof. At its rearward end, each of the side walls 133 and 134 is provided with a lateral extending, integral pivot pin. These pivot pins are shown at 140 and 141. The pivot pins 140 and 141 are adapted to be received in sockets within handle halves 121 and 122, one of these sockets being illustrated at 142 in FIGS. 25, 27 and 28. In this way, the trigger safety 5 is pivotally attached to the handle halves at the lower end of the notch 125 in the handle halves. Normally, the trigger safety 5 occupies its extended position illustrated in FIG. 3. In this position, the extension 136 of the trigger safety 5 engages and abuts the abutment surface 104 of trigger safety lockout 94. So long as the trigger safety 5 is in the position shown in FIG. 3, the trigger subassembly 3 cannot be pivoted to its actuated position and is maintained or locked in its unactuated position.

The handle snap lock 14 is illustrated in FIGS. 25 and 3. The handle snap lock 14 comprises an L-shaped member adapted to fit within the socket formed by interior walls 128 and 129 in right handle half 122 and corresponding walls in left handle half 121 (not shown). The handle snap lock has a forward end portion which extends through the slot 130 in the right handle half 122 and corresponding slot (not shown) in left handle half 121. This forward end of the handle snap lock 14 is hook-shaped, as shown at 143. It will be apparent from FIG. 3 that when the trigger assembly 3 is shifted to its fully actuated position adjacent handle assembly 4, the hooked end 143 of handle snap lock 14 will enter the slot in the bottom rear edge of the trigger assembly 3, formed by slot 111 in the left trigger cover 96 and slot 119 in the right trigger cover 97. Once it has entered this slot, it will lock the trigger assembly 3 in its fully actuated position, giving the surgeon a visual, audible and tractile indication that the instrument has been fully actuated and the surgical staples have been fully formed and implanted in the tissue being sutured.

Referring to FIGS. 3, 4, 13, 16 and 25, it will be apparent that when the cartridge/driver subassembly of FIG. 4 and the trigger subassembly 3 of FIG. 16 are joined together, along with the adjustment bolt/adjustment knob assembly of FIG. 13 (with the lugs 86 and 87 of the adjustment bolt 73 located, respectively, in elongated slots 63 and 57 of handle plates 19 and 18), the handle subassembly 4 of FIG. 25 can be added to this structure. The handle halves 121 and 122 are intended to surround the trigger subassembly 3 of FIG. 16, as well as the handle portions 51 and 59 of handle plates 18 and 19. The assembly of the elements illustrated in FIGS. 4, 13, 16 and 25 constitutes the primary or basic assembly of the instrument 1. The remaining subassembly of instrument 1 is partially illustrated in the exploded view of FIG. 30.

This final subassembly comprises a left hook 144 and a mirror image right hook 145 (see FIG. 3), a left body half 146 and a mirror image right body half 147 (see FIG. 3), a pilot 148, anvil 7, a left indicator slide 150 and a mirror image right indicator slide 150a (FIG. 3), a left indicator slide spring 151 and a corresponding right indicator spring 151a (FIG. 3), a left indicator spring cover 152 and an identical right indicator spring cover (not shown), a left indicator label 153 and a mirror image right indicator label (not shown), a slide crank 154, a knob lockout 155, an alignment and retaining pin 10 and an alignment and retaining pin knob 11.

The left hook 144 comprises a metallic member having an elongated shank 158. At its rearward end, the elongated shank 158 terminates in a portion 159 parallel to the remainder of the shank, but slightly offset as at 160. At its rearwardmost end, the shank portion 159 contains an elongated perforation 161. At its forward end, the shank 158 terminates in a hook-like structure 162, the forwardmost portion 163 of which constitutes a part of fixed jaw 6. The portion 163 is parallel to the portion 162 and the shank portion 158, but is slightly offset therefrom as at 164. It will be understood that the right hook 145 (see FIG. 3) is a mirror image of left hook 144.

The left body half 146 is illustrated in FIGS. 30, 31 and 32. Left body half 146 is molded of plastic and is essentially hollow, having along its inner edges a plurality of elongated lugs 164 intended to be received in corresponding grooves formed in the edges of right body half 147, the body halves being intended to be joined together by gluing, ultrasonic welding or the like.

Along its bottom edge, the body half 146 has an elongated notch 165. Body half 147 has a similar notch shown at 166 in FIG. 3. The notches 165 and 166 form an elongated rectangular opening, adapted to receive the upper end of the handle assembly, as will be evident hereinafter. On its upper surface, body half 146 has a similar, elongated, rectangular notch 167. A corresponding notch is provided at 168 in body half 147 (see FIGS. 2 and 3). The notches 167 and 168 define a rectangular opening at the top of the instrument body, partially shown in FIG. 2 and generally indicated at 169.

At its rearward end, body half 146 is provided with a semi-circular notch 170. A similar semi-circular notch is provided at 171 in body half 147 (see FIG. 3). When the adjustment knob 12 is mounted within the body, as shown in FIG. 3, the semi-circular notches 170 and 171 surround and engage the annular notch 77 in the adjustment knob 12, thereby both captively and rotatively mounting the adjustment knob 12 within the body 2.

Referring to FIGS. 2, 3, 31 and 32, the upper surface of body half 146 is provided with a pair of upstanding lugs 172 and 173. Body half 147 is provided with a corresponding pair of upstanding lugs 174 and 175. As will be noted from FIG. 32, the lower portions 172a and 172b of lugs 172 and 173 are slightly inset. The same is true of the lugs 174 and 175 on body half 147. Thus, when body halves 146 and 147 are joined together, the upper portions of lugs 172 and 174 are joined, as are the upper portions of lugs 173 and 175 (see FIG. 2). The lower inset portions of these lugs form passages through the lug pairs for the alignment and retaining pin 10, as can be seen in FIG. 3.

Reference is now made to FIG. 33 wherein the pilot 148 is illustrated. The pilot 148 comprises a molded plastic member having a body portion 176 similar in shape to the jaw portion 163 of the left hook 144. The pilot portion 176 is provided with three perforations 177, 178 and 179. It will be noted that the portion 163 of the left hook 144 (see FIG. 30) is provided with three corresponding perforations 180, 181 and 182. The right hook 145 (FIG. 3) is provided with a similar set of perforations (not shown).

The top front and bottom edges of the pilot portion 176 is provided with a flange 183 which extends laterally to either side of the body portion 176. Near its upper end, the body portion 176 is provided with a clearance notch 184 to accommodate the forward end of the alignment and retaining pin 10, as will be evident hereinafter. To complete the pilot 148, the body portion 176 thereof is provided with a rearwardly extending shank 185. The purpose of this shank will also be apparent hereinafter.

FIGS. 4, 35 and 36 illustrate the anvil 7 of the present invention. As is evident from FIG. 36, the anvil 7 is of inverted U-shaped configuration, having an anvil surface 186 and a pair of downwardly depending legs 187 and 188. As will be seen from FIG. 34, the legs 187 and 188 have a configuration similar to the body portion 176 of pilot 148. It will be noted that leg 188 in FIG. 34 is illustrated as having three perforations 198, 190 and 191. These perforations correspond to the perforations 177, 178 and 179 in pilot 148 and to the perforations 180, 181 and 182 in the hook 144 (see FIG. 30). Anvil leg 187 is provided with a corresponding set of perforations (not shown).

Turning to FIG. 35, the anvil surface 186 has at one end a perforation 192 to accommodate the alignment and retaining pin 10, as will be described hereinafter. At its other end, the anvil surface has an elongated opening 193 adapted to accommodate the shank 185 of pilot 148.

The anvil surface 186 of anvil 7 is provided with two longitudinally extending rows 194 and 195 of pairs of staple forming pockets. The pockets of row 194 are staggered with respect to the pockets of row 195. As a result, the instrument of the present invention will provide, in the embodiment described, two rows of staples in the tissue being sutured, the staples of each row being staggered with respect to the other. FIG. 37 illustrates an exemplary pair of pockets 196–197.

The pockets 196 and 197 are illustrated as being of the type taught in U.S. Pat. No. 4,319,576. To this end, the pockets 196 and 197 are mirror images of each other and are otherwise identical. The pockets 196 and 197 each have first longitudinally extending large radius portions 196a and 197a, respectively. The large radius portions cooperate with the points of the legs of a surgical staple and cause them to bend toward each other. The anvil pockets 196 and 197 also have longitudinally extending smaller radius portions 196b and 197b, respectively. As the staple legs are driven further toward the anvil, The small radius anvil pocket portions 196b and 197b will cause the staple legs to form a radius of curvature of their own, forming the staple into a B-shape. The configuration of anvil pockets 196 and 197 allows the instrument of the present invention to be provided with a single staple size which will be adequately clinched throughout the working gap of the instrument.

Figure 10:
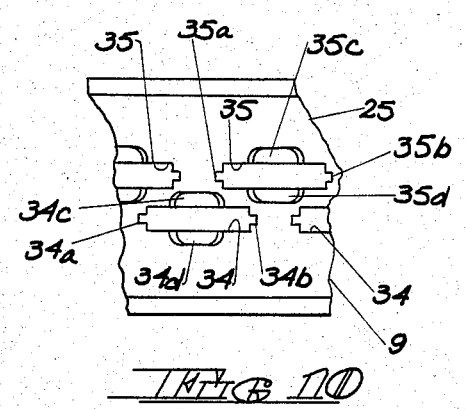
FIG. 10 is a fragmentary, enlarged front view of the cartridge of FIGS. 7 through 9.
Figure 14H:
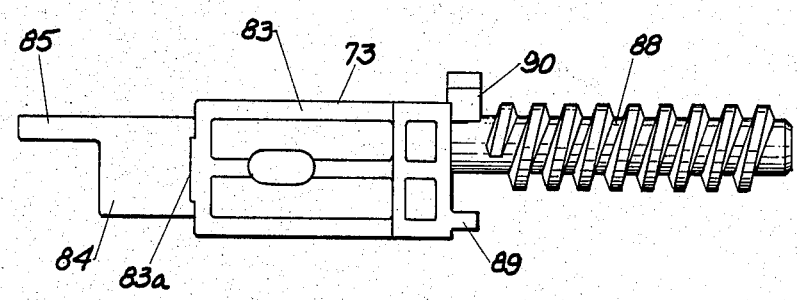
FIGS. 14 and 15 are, respectively, a side elevational view and a plan view of the adjustment bolt of the present invention.
Figure 15:
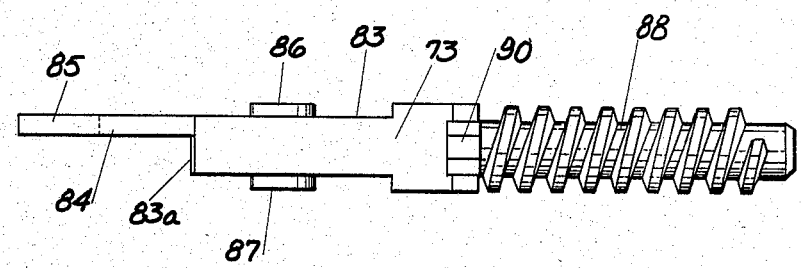

At this point reference is made to FIG. 10 illustrating the forward surface of cartridge 9. It will be noted that each of the staple retaining slots 34 is provided with depressions 34c and 34d to either side thereof. Similarly, each of the staple retaining slots 35 is provided with depressions 35c and 35d to either side thereof. The purpose of these depressions is to accommodate the free ends of the surgical staples when the minimum gap of the instrument is used.

Reference is now made to FIGS. 2, 3, 30 and 32. Turning first to FIG. 32, it will be noted that the left hook 144 is illustrated in broken lines in association with body half 146. The shank portions 158 and 159 of left hook 144 lie along the inside surface of body half 146. The body half 146 is provided with a lug 198 which is received in the perforation 161 in the rearward end of the hook shank portion 159. It will be understood that the right hook 145 will be similarly associated with the right body half 147.

Turning to FIGS. 3 and 30, the anvil 7 is placed upon pilot 148, with the anvil legs 187 and 188 extending to either side of the pilot body portion 176, the edges of anvil legs 187 and 188 lying adjacent the pilot flange 183. The pilot shank 185 extends through the elongated opening 193 of the anvil 7.

When the body halves 146 and 147 are joined together, along with their associated left hook 144 and right hook 145, the assembly of pilot 148 and anvil 7 is located between the portion 163 of left hook 144 and the corresponding portion of right hook 145. This portion 163 of left hook 144, the pilot 148, the anvil 7 and the portion of right hook 145 corresponding to left hook portion 163 constitute the fixed jaw 6 of FIG. 1. These elements are joined together by rivets 199, 200 and 201, as shown in FIGS. 3 and 30. The rivets pass through the above described corresponding perforations in these elements.

Turning to FIGS. 1, 3 and 4, the movable jaw of the instrument, generally indicated at 8 in FIG. 1, comprises the cartridge 9, the casing 16 and those elements within casing 16 including driver 15, the plate-like portion 49 of driver rod 17, and the plate-like portions 52 and 60 of the left and right handle plates 18 and 19. As is most clearly shown in FIG. 3, the shank 185 of pilot 148 extends through the elongated opening 28 of cartridge 9 and the elongated opening 45 of casing 16, thereby acting as a guide for these elements as they are shifted toward and away from the anvil 7.

Through the agency of the left and right handle plates 18 and 19, the trigger assembly of FIG. 16 and the handle assembly of FIG. 25 constitute a part of movable jaw 8 and, therefore, must be shiftable within the body halves 146 and 147 with the movable jaw 8. To this end, reference is made to FIGS. 25 and 26. It will be remembered that right handle half 122 is provided at its upper end with a longitudinally extending groove 131. As will be apparent from FIG. 25, the upper end of mirror image left handle half 121 is provided with an identical groove 131a. It will further be remembered (see FIGS. 3 and 32) that the body halves 146 and 147 have elongated notches 165 and 166 formed in their lower surfaces, defining a rectangular opening to receive the upper end of the handle/trigger assembly. The longitudinal edges of the notches 165 and 166 engage the longitudinal slots 131a and 131, respectively, of handle halves 121 and 122 with a sliding engagement.

Reference is now made to FIG. 3. It will be evident from FIG. 3 that when adjustment knob 12 is rotated in a clockwise direction, the threaded engagement of bore 80 of knob 12 and bolt shaft 88 will cause the adjustment bolt 73 to shift forwardly with respect to adjustment knob 12. Adjustment bolt 73 is connected to the left handle plate 18 and right handle plate 19 via lug 87 on adjustment bolt 73 to hole 57 on left handle plate 18 and lug 86 on adjustment bolt 73 to hole 63 on right handle plate 19. This will result in forward movement of the handle and trigger assembly, as well as the movable jaw 8. In this way, the movable jaw 8 and its cartridge 9 will be brought toward anvil 7 to a distance therefrom within the working gap of the instrument.

The instrument of the present invention is provided with indicator means in association with each body half 146 and 147 enabling the surgeon to visually determine when the distance between anvil 7 and cartridge 9 is within the working gap of the instrument and just what region of the working gap it is within.

Reference is made to FIGS. 1, 30, 31 and 32 with respect to which the indicator means in association with left body half 146 will be described. It will be understood that the indicator means in association with right body half 147 is a mirror image thereof, and otherwise identical thereto. Provision of indicator means in assocation with both body halves 146 and 147 assures that one or the other of the indicator means will be readily readable by the surgeon, regardless of the position of the instrument during use.

Left body half 146 is provided with an elongated, rectangular depression or opening 202. A portion 202a of the opening extends through the body half 146. The opening 202 is provided with an upper inwardly extending wall 203, a lower inwardly extending wall 204 and an inwardly extending end wall 205. A second portion 202b of opening 202 is provided with a rear wall 206, joining the innermost edges of walls 203, 204 and 205. The forward portion 202b of recess 202 is surrounded by a shallow depression, forming a surrounding shoulder 207, the purpose of which will be apparent hereinafter. As is most clearly shown in FIG. 32, the bottom wall 204 extends nearly to the rearward end of body half 146. Adjacent the end of bottom wall 204 there is an integral molded stop 208. The bottom wall 204 is also provided with an upstanding guide 209 near its innermost edge.

The recess 202 is intended to have the slide indicator 150 mounted therein. The slide indicator 150 is shown in FIGS. 30 and 38. Slide indicator 150 comprises an elongated molded plastic member having a planar inner surface 210 and a planar outer surface 211. The indicator slide terminates in a forward end 212 and a rearward end 213. The planar inner surface 210 is provided with an inwardly extending lug 214. The planar outer surface 211 has a raised indicator or indicia line 215.

The indicator slide 150 is located within recess 202 and is slidable therein. At least that portion of the inner surface 150 adjacent the forward end 212 lies against the wall 206. The planar inner surface 210 is also always in contact with guide 209. The indicator slide 150 is shiftable forwardly within recess 202 until its stop lug 214 engages the free end of rear wall 206. The slide 150 is shiftable rearwardly within the recess until its rearward end 213 abuts stop 208 of body half 146. The slide spring 151, shown in FIG. 30, is located in that portion 202b of recess 202 with its forward end abutting wall 205 and its rearward end abutting the forward end 212 of indicator slide 150. In this way, indicator slide 150 is biased to its rearwardmost position against stop 208.

A spring cover is provided for recess portion 202b. The cover is shown at 152 in FIG. 30. The cover is so sized as to be received on the surrounding shoulder 207 about recess portion 202b and is permanently affixed thereto by gluing, ultrasonic welding or the like. The cover 152 is made of plastic material and is of a thickness such that, when mounted in place, its outer surface will be flush with the surrounding outer surface of body half 146. With spring cover 152 in place, the slide spring 151 and the indicator slide 150 are captively mounted in body half 146.

To complete the indicator structure of body half 146, a label 153 is provided. The label 153 has a window 216. A comparison of FIGS. 1 and 31 will show that the window is so located as to overlie a part of that portion 202a of depression or opening 202 in body half 146.

Above window 216, label 153 is provided with indicia 217 which define the working gap of the instrument 1. Additional numerical indicia 218 may be provided corresponding to tissue thickness readings from tissue thickness measuring instrument such as that taught in U.S. Pat. No. 4,312,363.

As indicated above, in instruments of this general type, it was common for the prior art to provide the instrument either with a cartridge of staples with short legs to form tight sutures or a cartridge with staples having longer legs for looser sutures when suturing thicker tissue. The label 153 may be provided with an indicia mark 219 which would indicate to the surgeon at a glance that he was within that portion of the instrument gap which would in prior art terms require a tight or shorter legged staple and an indicia mark 220 which would indicate to the surgeon at a glance that he was within that part of the instrument gap requiring the equivalent of a prior art loose or longer legged staple. Other indicia means may be provided on label 153, as desired.

It will be understood by one skilled in the art that body half 147 is provided with a recess or opening equivalent to recess or opening 202, but a mirror image thereof. The second body half 147 will also have an indicator slide 150a identical to indicator slide 150, a slide spring 151b identical to slide spring 151 and a spring cover (not shown) identical to cover 152. Finally, a label constituting a mirror image of label 153 will be affixed to body half 147.

In FIG. 1, the indicator line 215 of indicator slide 150 is shown in that position which it would normally occupy when the slide 150 is in its normal, rearwardmost position as urged by slide spring 151, and when the movable jaw 8 is at or near its maximum spacing from fixed jaw 6 and cartridge 9 is spaced from anvil 7 by a distance considerably greater than the working gap of the instrument. Means are provided to shift the indicator slide 150 and its counterpart 150a in association with body half 147 so that they will cooperate with the indicia on label 153 (and the corresponding label on body half 147) when the working gap of the instrument is achieved. This means is illustrated in FIGS. 30, 39, 40 and 41 in the form of an indicator slide crank 154.

Indicator slide crank 154 comprises an inverted U-shaped member having a base portion 221 from which a pair of parallel spaced legs 222 and 223 depend. The base portion 221 terminates at its ends in pivot pins 224 and 225. The downwardly depending leg 223 has at its free end an abutment surface 226 adapted to abut and shove against the inwardly extending lug 214 of indicator slide 150. The leg 222 terminates at its free end in a similar abutment surface 227 adapted to abut and shove against the inwardly extending lug 150b of indicator slide 150a. This is illustrated in FIG. 3. To complete the indicator slide crank 154, a cylindrical brace 228 extends between legs 222 and 223 in parallel-spaced relationship to base portion 221.

It will be noted from FIG. 32 that body half 146 has a socket 229 formed therein near its upper rearward end. Socket 229 is intended to receive pivot pin 225 of indicator slide crank 154. It will be understood that body half 147 will be provided with a similar socket (not shown) for the receipt of pivot pin 224 of indicator slide crank 154. In this way, the indicator slide crank 154 is pivotally mounted within body halves 146 and 147, as shown in FIG. 3. The legs 222 and 223 of the indicator slide crank 154 straddle the main body portion 83 of adjustment bolt 73.

In FIG. 3, the indicator slide crank 154 is illustrated in its normal position with its abutment surface 227 engaging the inwardly extending lug 150b of indicator slide 150a. It will be understood that the other abutment surface 226 of indicator slide crank 154 will lie in abutment with the inwardly extending lug 214 of indicator slide 150. As will be apparent from FIG. 3, as the adjustment knob 12 is turned in a clockwise direction, resulting in forward movement of adjustment bolt 73 (and thus forward movement of movable jaw 8 toward fixed jaw 6), the upstanding lug 90 of bolt 73 will approach the cylindrical brace 228 of the indicator slide crank 154. The upstanding lug 90 will contact cylindrical brace 228 at a point where movable jaw 8 has approached fixed jaw 6 to the extent that the distance between cartridge 9 and anvil 7 is just slightly greater than the operating gap of the instrument. Further forward movement of adjustment bolt 73 will cause the upstanding bolt lug 90 to rotate indicator slide crank 154. This, in turn, will result in the forward shifting of indicator slides 150 and 150a against the action of slide springs 151 and 151a. When the operating gap is reached, the indicia lines of indicator slides 150 and 150a will register with their respective scales or indicia marks on label 153 and its counterpart in association with body half 147. This registration will continue throughout the operating gap of the instrument. The indicator slide crank 154 is so configured that its rotation will cause longitudinal movement of indicator slides 150 and 150a four times greater than the corresponding movement of cartridge 9 toward anvil 7. This movement magnification of the indicator slides 150 and 150a enables the indicia on the labels to be larger and more legible.

As indicated above, the alignment and retaining pin 10 is slidably mounted in lug pairs 172-174 and 173-175 on the upper surface of the instrument. The rearward end of alignment and retaining pin 10 is affixed to the knob 11 illustrated in FIGS. 1, 2, 3, 30 and 45. The knob 11 is provided with an upstanding lug 230 by which it can be easily manually manipulated.

In FIG. 3, the alignment and retaining pin 10 is illustrated in its normal, retracted position. In this position, it will be noted that the forwardmost end of the alignment and retaining pin 10 is located within casing 16, passing through perforation 43 in casing 16. Once the tissue to be sutured is located between the fixed jaw 6 and movable jaw 8, the alignment and retaining pin 10 is shoved forwardly by means of knob 11. This causes the forward end of the alignment and retaining pin to pass through the perforation 27 in cartridge 9, the perforation 192 in anvil 7 and into the clearance notch 184 in pilot 148. In its extended position just described, the alignment and retaining pin 10 accomplishes two purposes. First of all, it assures proper alignment of anvil 7 and cartridge 9 so that the staples will be properly aligned with and clinched by the pairs of anvil pockets when the instrument is actuated. Furthermore, the alignment and retaining pin 10 spans the distance between the fixed jaw 6 and the movable jaw 8 (i.e., between cartridge 9 and anvil 7), assuring that tissue located therebetween will remain therebetween during operation of the instrument.

It is very important that, once the tissue to be sutured has been located between cartridge 9 and anvil 7, the alignment and retaining pin 10 be shifted to its extended position before the movable jaw 8 is shifted toward fixed jaw 6 by adjustment knob 12. To this end, an adjustment knob lockout means is provided, preventing rotation of adjustment knob 12 unless and until the alignment and retaining pin 10 has been shifted to its forwardmost position.

The adjustment knob lockout 155, as shown in FIG. 42, is a molded plastic member comprising a first portion 231 which is substantially planar and has a forward end 232. The portion 231 has a longitudinally extending groove 233 centrally located thereon, the groove 233 terminating in a forward abutment surface 234. The portion 231 is also provided with thin lateral flanges 235 and 236.

At its rearward end, the portion 236 terminates in an upwardly extending portion 237. This portion, in turn, terminates in a substantially planar portion 238 offset from and parallel to the portion 231. The portion 238, in turn, terminates in a slightly narrower lug 239 so configured as to be receivable within the notch 78 of adjustment knob 12 (see FIG. 13).

Returning to FIG. 32, the body half 146 adjacent notch 167 is provided with a longitudinal groove 239. Groove 239 is intended to receive flange 235 of adjustment knob lockout 155. It will be understood that the other body half 147 will be provided with a similar groove (not shown) adjacent notch 168 formed in its upper surface. The groove in body half 147 is intended to receive adjustment knob lockout flange 236.

In this manner, adjustment knob lockout 155 is shiftably mounted within body halves 146 and 147, as shown in FIG. 3. As is shown in FIG. 2, the portion 231 of adjustment knob lockout 155 is exposed in the opening 169 in the body 2 formed by body half notches 167 and 168.

In FIG. 3, the adjustment knob lockout 155 is illustrated in its fully retracted position, with its rearward lug portion 239 engaged in the notch 78 of adjustment knob 12, precluding rotation of the adjustment knob. It will be noted that the portion 238 of the adjustment knob lockout 155 passes between the base portion 221 and the cylindrical brace 228 of indicator slide crank 154. It will be further noted that the portion 238 of the adjustment knob lockout 155 is supported by a tab 239a located on the inner surface of left body half 146 (FIG. 32) and a corresponding tab on the inner surface of right body half 147 (not shown). The purpose of these tabs is to guide adjustment knob lockout 155 as it travels.

Turning to FIG. 45, it will be noted that the alignment and retaining pin knob 11 has a downwardly depending lug 240. As will be apparent from FIG. 3, this lug 240 extends into the longitudinal groove 233 of the forward portion 231 of adjustment knob lockout 155.

Thus, when the alignment and retaining pin 10 is shoved to its forwardmost position by knob 11, the knob lug 240 will shift forwardly within the adjustment knob lockout groove 233 until it contacts abutment surface 234. Further forward movement of knob 11 will shift the adjustment knob lockout 155 forwardly, removing its rearward lug portion 239 from the notch 78 of adjustment knob 12, enabling the adjustment knob 12 to be rotated. This arrangement assures the proper sequence of events, requiring the alignment and retaining pin 10 to be shoved to its forwardmost position before the adjustment knob 12 can be rotated.

The adjustment knob lockout 155 serves one additional purpose. In FIG. 2, the adjustment knob lockout 155 is shown in its forwardmost position, even though alignment and retaining pin knob 11 is shown in its retracted position. It will be evident that in its forwardmost position, the adjustment knob lockout 155 closes all but the forwardmost portion of the opening 169 in the top of body 2. FIG. 3 illustrates the instrument of the present invention in its initial condition, as it would be received by the surgeon. It will be noted that the upstanding lug 136 of trigger safety 5 is engaged with the abutment surface 104 of trigger safety lockout 94. In order for the trigger safety 5 to release trigger subassembly 3, it is necessary that it be rotated to its folded position within the handle subassembly 4. This cannot be done until the trigger safety lockout 94 can be shifted upwardly to release the lug 136 of trigger safety 5. It will be remembered from FIGS. 16 and 18 that the uppermost end of trigger safety lockout 94 is provided with an extension 107. With the parts in their positions shown in FIG. 3, any attempt to shift the trigger safety lockout 94 upwardly against the action of spring 95 would be precluded by abutment of the trigger safety lockout extension 107 against the underside of the adjustment knob lockout 155. However, when the adjustment knob 12 has been rotated sufficiently to cause movable jaw 8 toward fixed jaw 6 with cartridge 9 spaced from anvil 7 by a distance just slightly greater than the maximum working gap of the instrument, the extension 107 of trigger safety lockout 94 will clear the forwardmost end 232 of adjustment knob lockout 155. As a result of this, upward pressure applied to the trigger safety 5 will shift the trigger safety lockout 94 upwardly against the action of spring 95 by an amount sufficient to clear the lug 136 of trigger safety 5, enabling the trigger safety 5 to pivot to its inactive position nested within handle subassembly 4. From this point on, the surgeon is free to actuate the trigger subassembly 3 to implant and form a double row of staples in the tissue located between movable jaw 8 and fixed jaw 6.

The instrument and its parts having been described in detail, the manner of use can be set forth as follows. The instrument 1 is brought to the surgical environment in packaged and pre-sterilized condition. Instrument 1 is also in its opened condition as illustrated in FIGS. 1 and 3, with the movable jaw 8 retracted from fixed jaw 6 and the cartridge 9 spaced from anvil 7 by the maximum distance. The adjustment knob lockout 155 is in its locking position with its lug portion 239 located within the slot 78 of adjustment knob 12. The alignment and retaining pin 10 is in its fully retracted position and trigger safety 5 is in its trigger assembly locking position, again all as is shown in FIGS. 1 and 3. The tissue to be transected or resected is positioned between the movable jaw 8 and fixed jaw 6 (i.e., between the cartridge 9 and anvil 7).

Next, the surgeon shifts the alignment and retaining pin 10 forwardly by means of knob 11, to cause the forward end of the alignment and retaining pin 10 to pass through the cartridge 9, anvil 7 and into the clearance notch 184 of the pilot 148. This action accomplishes three purposes. First of all, it assures proper alignment between the cartridge 9 and anvil 7. Secondly, it assures that the tissue between the jaws 6 and 8 will remain there. Finally, the shifting of the alignment and retaining pin 10 to its fully actuated position will shift the adjustment knob lockout 155 to its forward position, releasing the adjustment knob 12.

Thereafter, the surgeon rotates the adjustment knob 12 until the cartridge 9 is spaced from anvil 7 by the desired distance within the working gap of instrument 1, as indicated by the above described indicator means to either side of instrument body 2. The setting of the proper gap for the tissue being sutured is accomplished by the surgeon either based upon his own experience, or through the use of a surgical tissue thickness measuring instrument of the type, for example, set forth in the above noted U.S. Pat. No. 4,312,363. Furthermore, indicator indicia 219 corresponds to an approximate closed staple height of 1.5 mm, while indicator 220 corresponds to an approximate closed staple height of 2.0 mm. These closed staple heights are typical of those provided by various prior art instruments and the indicator indicia 219 or 220 can be used by the surgeon as a guide in gap setting.

The appropriate gap within the working gap of the instrument having been set, the instrument is ready for actuation. The trigger assembly 3 and handle assembly 4 will have shifted forwardly with respect to the body 2 by an amount sufficient to place the trigger safety lockout 94 in a position to release trigger safety 5. Therefore, the surgeon releases trigger safety 5 and then actuates trigger assembly 3, pulling it back firmly to the handle assembly 4. When this is done properly, hooked end 143 of handle snap lock 14 will enter slot portions 111 and 119 of trigger assembly 3, engaging trigger subassembly 3 and locking it in its actuated position. This provides the surgeon with a visual, tactile and audible indication that the instrument 1 has been properly actuated and the surgical staples have been properly implanted and formed in the tissue being sutured.

Prior to removal of instrument 1, several edges adjacent the tissue may be used as a cutting guide to transect the tissue, or to excise any margin of tissue protruding through the jaws. This will aid in cutting the tissue at a proper distance from the staple line.

Thereafter, the instrument is opened by rotating the adjustment knob 12 in a counter-clockwise direction and shifting knob 11 of alignment and adjustment pin 10 to its retracted position. Thereafter, the instrument may be disposed of in any appropriate manner.

Modifications may be made in the invention without departing from the spirit of it. For example, the instrument of the present invention may be made in various sizes to produce rows of staples differing in the number of staples per row.

While the instrument has been described in terms of implanting and forming two rows of surgical staples, the staples of each row staggered with respect to the other, by simple modification of the anvil 7, cartridge 9 and driver 15, the instrument could be used to form and implant a single row of surgical staples.

The surgical stapling instrument of the present invention has been described in terms of the Figures as they appear in the drawings. Use of such terms as "forward", "rearward", "top", "bottom", and the like, both in the specification and claims, is simply for clarity of description and explanation. One skilled in the art will understand that the instrument may assume any appropriate position during use.

What is claimed is:

1. A linear surgical stapling instrument for forming and implanting at least one rectilinear row of surgical staples in the tissue of a patient, said instrument comprising an elongated body terminating at its forward end in a fixed jaw, an anvil mounted on said fixed jaw, a basic assembly slidably supported by said body and shiftable longitudinally thereof, said basic assembly comprising a movable jaw subassembly, a trigger subassembly, a handle subassembly and an adjustment bolt-adjustment knob subassembly all operatively joined together, said movable jaw subassembly comprising a cartridge containing at least one row of surgical staples and having a forward surface facing and parallel to said anvil, a hollow casing affixed to said cartridge, a driver for said staples slidably mounted within said casing, means to shift said driver within said casing between a retracted position and a staple driving position to drive said staples through the tissue and against said anvil over a range of distances between said cartridge and said anvil constituting the working gap of the instrument, said driver shifting means comprising an elongated driver rod having a forward end connected to said driver within said casing and a rearward end connected to said trigger assembly, said trigger assembly having an upper end pivotally affixed to said basic assembly and a lower free end, said trigger being pivotable between an unactuated position spaced from said handle assembly and wherein said driver is in said retracted position and an actuated position adjacent said handle assembly and wherein said driver is in said staple driving position, said adjustment bolt being affixed to said basic assembly within said body, said adjustment knob being captively and rotatably mounted at the rearward end of said body and being threadedly engaged with said adjustment bolt such that rotation of said adjustment knob in one direction will shift said adjustment bolt and said basic assembly rearwardly with respect to said body with said movable jaw assembly shifting away from said fixed jaw and said cartridge shifting away from said anvil, and rotation of said adjustment knob in the other direction will shift said basic assembly forwardly with respect to said body and said movable jaw assembly toward said fixed jaw and said cartridge toward said anvil, an alignment and retaining pin slidably mounted on said body, said alignment pin having a free forward end, said alignment pin being shiftable longitudinally of said body between a retracted position wherein said forward end of said pin lies within said casing and an extended position wherein said free end passes through coaxial perforations in said cartridge and said anvil and into a recess in said fixed jaw to assure proper alignment of said cartridge and said anvil, indicator means to indicate when the distance between said cartridge and said anvil is at and within said working gap of said instrument, and safety means to assure proper sequential operation of said instrument.

2. The instrument claimed in claim 1 wherein said safety means includes adjustment knob safety means preventing rotation of said adjustment knob when said alignment and retaining pin is in its retracted position.

3. The instrument claimed in claim 1 wherein said safety means includes trigger safety means preventing shifting of said trigger assembly from said unactuated to said actuated position unless the distance between said anvil and said cartridge is near said working gap.

4. The instrument claimed in claim 1 wherein said safety means includes trigger latch means to lock said trigger assembly in said actuated position to provide a visual, audible and tactile indication that said staples have been formed and implanted.

5. The instrument claimed in claim 1 wherein said indicator means comprises at least one window in said body, indicia on said body adjacent said window representing said working gap, at least one elongated indicator slide having an indicia mark thereon and being mounted within said body adjacent said at least one window and being shiftable longitudinally in said body between an unactuated rearwardmost position and a forwardmost position, means to bias said at least one indicator slide to its rearwardmost position, and means actuable by said adjustment bolt to shift said at least one indicator slide toward said forwardmost position with said indicator slide indicia mark cooperating with said indicia on said body to indicate when the distance between said anvil and said cartridge is at and within said working gap.

6. The instrument claimed in claim 5 wherein said means to shift said at least one indicator slide comprises a crank, said crank having one end pivotally mounted within said body, said crank having a second end engaged with said at least one slide, lug means on said adjustment bolt so positioned as to engage said crank when said adjustment bolt has been shifted forwardly of said body by said adjustment knob to the extent that said distance between said anvil and said cartridge is slightly greater than said working gap, said engagement of said crank by said adjustment bolt lug is such that further forward motion of said bolt will pivot said crank and shift said at least one indicator slide forwardly toward its forwardmost position so that said indicator slide indicia mark will cooperate with said indicia on said body to visually indicate when the distance between said cartridge and said anvil is at and within said working gap.

7. The instrument claimed in claim 1 wherein said indicator means comprises a window in each side of said body, indicia on said body adjacent each window representing said working gap, a pair of elongated indicator slides each having an indicator mark, each of said indicator slides being mounted within said body adjacent one of said windows and being shiftable longitudinally in said body between an unactuated rearwardmost position and a forwardmost position, means to bias each of said indicator slides to their rearwardmost positions, and means actuable by said adjustment bolt to shift both of said indicator slides simultaneously and equally toward their forwardmost positions with said indicator mark of each of said indicator slides cooperating with its respective indicia on said body to simultaneously indicate when the distance between said anvil and said cartridge is at and within said working gap.

8. The instrument claimed in claim 7 wherein said means to shift said indicator slides comprises a crank, said crank comprising an inverted U-shaped member having a base portion and a pair of downwardly depending legs, said base portion being pivotally mounted in said body with said legs straddling said adjustment bolt, each of said crank legs terminating in an abutment surface engaging one of said indicator slides, lug means on said adjustment bolt so positioned as to engage said crank when said adjustment bolt has been shifted forwardly of said body by said adjustment knob to the extent that said distance between said anvil and said cartridge is slightly greater than said working gap, said engagement of said crank by said adjustment bolt lug is such that further forward motion of said bolt will pivot said crank and simultaneously shift said indicator slides forwardly toward their forwardmost positions so that said indicator slide indicia marks will cooperate with their respective indicia on said body to visually indicate when the distance between said cartridge and said anvil is at and within said working gap.

9. The instrument claimed in claim 8 wherein said crank is so configured as to shift said slides a distance four times greater than the distance said cartridge is simultaneously shifted by said adjustment knob.

10. The instrument claimed in claim 1 including first and second handle plates, said second handle plate comprising substantially a mirror image of said first handle plate, said first and second handle plates each comprising an elongated shank portion, said handle plate shank portions extending longitudinally within said body in parallel-spaced relationship to said driver rod and to either side thereof, said handle plate shank portions terminating at their forward ends in plate-like end portions located within said casing to either side of said driver rod forward end and said driver, said handle plate shank portions terminating at their rearward ends in enlarged portions in parallel-spaced relationship within said body, said enlarged portions having downwardly depending handle portions in parallel-spaced relationship to each other and located within said handle assembly, said trigger assembly being attached to said first and second handle plates between said enlarged portions thereof by a pivot pin, said adjustment bolt being affixed to said first and second handle plates between said enlarged portions thereof.

11. The instrument claimed in claim 10 including an actuating knob affixed to the rearward end of said alignment and retaining pin, said body having an elongated opening in the top thereof, an elongated adjustment knob lockout member being slidable longitudinally within said opening between a normal rearward position and a forward actuated position, said lockout member having a longitudinal groove therein terminating in an abutment surface near the forward end of said lockout member, said adjustment knob having an annular portion within said body, said annular portion having a radial notch formed in its peripheral surface, said lockout member having a rearward extension engagable in said notch when said lockout is in its normal rearward position to lock said adjustment knob, said alignment and retaining pin knob overlying said top opening in said body and said lockout member therein, said alignment and retaining pin knob having a downwardly depending lug extending into said lockout member groove, said lug being so configured and located as to shift forwardly in said groove and contact said abutment surface to shift said lockout member forwardly in said top body opening and shift said lockout member rearward extension out of said adjustment knob notch to unlock said adjustment knob when said alignment and retaining pin is shifted to its extended position.

12. The instrument claimed in claim 10 wherein said trigger assembly comprises an elongated planar trigger having an enlarged upper end and a shank portion, a pair of first and second covers surrounding said trigger shank portion and having mating edges joined together, said first cover having an upper end and an extension thereon operatively engaging said rearward end of said driver rod, said enlarged upper end of said trigger abutting said rearward end of said driver rod, a pivot pin within said body and mounted within said basic assembly, said pivot pin passing through coaxial perforations in said first cover extension and said enlarged upper end of said trigger, an elongated trigger lockout member being mounted within said trigger assembly adjacent said trigger, said trigger lockout member being shiftable longitudinally within said trigger assembly between lower and upper positions, resilient means within said trigger assembly biasing said trigger lockout member to said lower position, said trigger lockout member having an upper end with an extension thereon, said trigger lockout extension passing through a notch in said second cover and extending upwardly in said body, said trigger lockout member having an abutment shoulder about midway of its length, said first and second covers having substantially coplanar surfaces facing said handle assembly, means in said surfaces exposing said trigger lockout member abutment shoulder, said handle assembly having a surface facing said trigger, said handle assembly surface having an opening therein, an elongated trigger safety having a rearward end pivoted to said handle assembly and a forward end having an upstanding lug, said trigger safety being pivotal between an unactuated position nested in said handle assembly opening and substantially flush with said handle assembly surface and an actuated position extending toward said trigger assembly with said trigger safety lug engaging said trigger lockout member abutment shoulder to prevent actuation of said trigger assembly, abutment means so positioned within said body as to be contactable by said trigger lockout member extension to prevent longitudinal shifting of said trigger lockout member to said upper position to release said trigger safety until said basic assembly has been shifted forwardly of said body by said adjustment knob to the extent approaches said working gap.

13. The instrument claimed in claim 10 wherein said trigger assembly has a longitudinal surface facing said handle assembly, said trigger assembly having a transverse slot formed in said surface near said trigger assembly free end, said handle assembly having a hook-shaped trigger latch means, said trigger latch means being so configured and positioned as to enter said trigger assembly slot when said trigger is shifted to its actuated position to lock said trigger assembly in its actuated position as a visual, audible and tactile indication that said surgical staples have been formed and implanted in said tissue.

14. The instrument claimed in claim 1 including an actuating knob affixed to the rearward end of said alignment and retaining pin, said body having an elongated opening in the top thereof, an elongated adjustment knob lockout member being slidable longitudinally within said opening between a normal rearward position and a forward actuated position, said lockout member having a longitudinal groove therein terminating in an abutment surface near the forward end of said lockout member, said adjustment knob having an annular portion within said body, said annular portion having a radial notch formed in its peripheral surface, said lockout member having a rearward extension engageable in said notch when said lockout is in its normal rearward position to lock said adjustment knob, said alignment and retaining pin knob overlying said top opening in said body and said lockout member therein, said alignment and retaining pin knob having a downwardly depending lug extending into said lockout member groove, said lug being so configured and located as to shift forwardly in said groove and contact said abutment surface to shift said lockout member forwardly in said top body opening and shift said lockout member rearward extension out of said adjustment knob notch to unlock said adjustment knob when said alignment and retaining pin is shifted to its extended position.

15. The instrument claimed in claim 1 wherein said trigger assembly comprises an elongated planar trigger having an enlarged upper end and a shank portion, a pair of first and second covers surrounding said trigger shank portion and having mating edges joined together, said first cover having an upper end and an extension thereon operatively engaging said rearward end of said driver rod, said enlarged upper end of said trigger abutting said rearward end of said driver rod, a pivot pin within said body and mounted within said basic assembly, said pivot pin passing through coaxial perforations in said first cover extension and said enlarged upper end of said trigger, an elongated trigger lockout member being mounted within said trigger assembly adjacent said trigger, said trigger lockout member being shiftable longitudinally within said trigger assembly between lower and upper positions, resilient means within said trigger assembly biasing said trigger lockout member to said lower position, said trigger lockout member having an upper end with an extension thereon, said trigger lockout extension passing through a notch in said second cover and extending upwardly in said body, said trigger lockout member having an abutment shoulder about midway of its length, said first and second covers having substantially coplanar surfaces facing said handle assembly, means in said surfaces exposing said trigger lockout member abutment shoulder, said handle assembly having a surface facing said trigger, said handle assembly surface having an opening therein, an elongated trigger safety having a rearward end pivoted to said handle assembly and a forward end having an upstanding lug, said trigger safety being pivotable between an unactuated position nested in said handle assembly opening and substantially flush with said handle assembly surface and an actuated position extending toward said trigger assembly with said trigger safety lug engaging said trigger lockout member abutment shoulder to prevent actuation of said trigger assembly, abutment means so positioned within said body as to be contactable by said trigger lockout member extension to prevent longitudinal shifting of said trigger lockout member to said upper position to release said trigger safety until said basic assembly has been shifted forwardly of said body by said adjustment knob to the extent that the distance between said anvil and said cartridge approaches said working gap.

16. The instrument claimed in claim 1 wherein said trigger assembly has a longitudinal surface facing said handle assembly, said trigger assembly having a transverse slot formed in said surface near said trigger assembly free end, said handle assembly having a hook-shaped trigger latch means, said trigger latch means being so configured and positioned as to enter said trigger assembly slot when said trigger is shifted to its actuated position to lock said trigger assembly in its actuated position as a visual, audible and tactile indication that said surgical staples have been formed and implanted in said tissue.

17. The instrument claimed in claim 1 wherein said instrument comprises a single use, disposable instrument.

18. A linear surgical stapling instrument for forming and implanting at least one rectilinear row of surgical staples in the tissue of a patient, said instrument comprising an elongated body terminating at its forward end in a fixed jaw, an anvil mounted on said fixed jaw, a basic assembly slidably supported by said body and shiftable longitudinally thereof, said basic assembly comprising a movable jaw subassembly, a trigger subassembly, a handle subassembly and an adjustment bolt-adjustment knob subassembly all operatively joined together, said movable jaw subassembly comprising a cartridge containing at least one row of surgical staples and having a forward surface facing and parallel to said anvil, a hollow casing affixed to said cartridge, a driver for said staples slidably mounted within said casing, means to shift said driver within said casing between a retracted position and a staple driving position to drive said staples through the tissue and against said anvil over a range of distances between said cartridge and said anvil constituting the working gap of the instrument, said driver shifting means comprising an elongated driver rod having a forward end connected to said driver within said casing and a rearward end connected to said trigger assembly, said trigger assembly having an upper end pivotally affixed to said basic assembly and a lower free end, said trigger being pivotable between an unactuated position spaced from said handle assembly and wherein said driver is in said retracted position and an actuated position adjacent said handle assembly and wherein said driver is in said staple driving position, said adjustment bolt being affixed to said basic assembly within said body, said adjustment knob being captively and rotatably mounted at the rearward end of said body and being threadedly engaged with said adjustment knob such that rotation of said adjustment knob in one direction will shift said adjustment bolt and said basic assembly rearwardly with respect to said body with said movable jaw assembly shifting away from said fixed jaw and said cartridge shifting away from said anvil, and rotation of said adjustment knob in the other direction will shift said basic assembly forwardly with respect to said body and said movable jaw assembly toward said fixed jaw and said cartridge toward said anvil, an alignment and retaining pin slidably mounted on said body, said alignment pin having a free forward end, said alignment pin being shiftable longitudinally of said body between a retracted position wherein said forward end of said pin lies within said casing and an extended position wherein said free end passes through coaxial perforations in said cartridge and said anvil and into a recess in said fixed jaw to assure proper alignment of said cartridge and said anvil, and indicator means to indicate when the distance between said cartridge and said anvil is at and within said working gap of said instrument.

19. The instrument claimed in claim 18 wherein said instrument comprises a single use, disposable instrument.

20. The instrument claimed in claim 18 wherein said indicator means comprises at least one window in said body, indicia on said body adjacent said window representing said working gap, at least one elongated indicator slide having an indicia mark thereon and being mounted within said body adjacent said at least one window and being shiftable longitudinally in said body between an unactuated rearwardmost position and a forwardmost position, means to bias said at least one indicator slide to its rearwardmost position, and means actuable by said adjustment bolt to shift said at least one indicator slide toward said forwardmost position with said indicator slide indicia mark cooperating with said indicia on said body to indicate when the distance between said anvil and said cartridge is at and within said working gap.

21. The instrument claimed in claim 18 wherein said indicator means comprises a window in each side of said body, indicia on said body adjacent each window representing said working gap, a pair of elongated indicator slides each having an indicator mark, each of said indicator slides being mounted within said body adjacent one of said windows and being shiftable longitudinally in said body between an unactuated rearwardmost position and a forwardmost position, means to bias each of said indicator slides to their rearwardmost positions, and means actuable by said adjustment bolt to shift both of said indicator slides simultaneously and equally toward their forwardmost positions with said indicator mark of each of said indicator slides cooperating with its respective indicia on said body to simultaneously indicate when the distance between said anvil and said cartridge is at and within said working gap.

22. The instrument claimed in claim 18 including first and second handle plates, said second handle plate comprising substantially a mirror image of said first handle plate, said first and second handle plates each comprising an elongated shank portion, said handle plate shank portions extending longitudinally within said body in parallel-spaced relationship to said driver rod and to either side thereof, said handle plate shank portions terminating at their forward ends in plate-like end portions located within said casing to either side of said driver rod forward end and said driver, said handle plate shank portions terminating at their rearward ends in enlarged portions in parallel-spaced relationship within said body, said enlarged portions having downwardly depending handle portions in parallel-spaced relationship to each other and located within said handle assembly, said trigger assembly being attached to said first and second handle plates between said enlarged portions thereof by a pivot pin, said adjustment bolt being affixed to said first and second handle plates between said enlarged portions thereof.

* * * * *